(12) United States Patent
Ellis

(10) Patent No.: US 11,210,784 B2
(45) Date of Patent: *Dec. 28, 2021

(54) SYSTEMS AND METHODS FOR IMAGING DISEASE BIOMARKERS

(71) Applicant: Neuroptica, LLC, Hoffman Estates, IL (US)

(72) Inventor: Matthew Paul Ellis, Hoffman Estates, IL (US)

(73) Assignee: NEUROPTICA, LLC, Hoffman Estates, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/092,051

(22) Filed: Nov. 6, 2020

(65) Prior Publication Data

US 2021/0090253 A1    Mar. 25, 2021

Related U.S. Application Data

(63) Continuation of application No. 16/986,097, filed on Aug. 5, 2020, now Pat. No. 10,878,568.
(Continued)

(51) Int. Cl.
| | | |
|---|---|---|
| G06T 7/00 | (2017.01) | |
| H04N 5/225 | (2006.01) | |
| A61B 5/0205 | (2006.01) | |
| A61B 5/377 | (2021.01) | |
| A61B 5/16 | (2006.01) | |
| A61B 5/00 | (2006.01) | |
| A61B 3/12 | (2006.01) | |
| G06K 9/46 | (2006.01) | |
| G06K 9/62 | (2006.01) | |
| G06K 9/20 | (2006.01) | |

(52) U.S. Cl.
CPC .......... *G06T 7/0012* (2013.01); *H04N 5/2256* (2013.01); *G06T 2207/10152* (2013.01); *G06T 2207/30041* (2013.01)

(58) Field of Classification Search
USPC .................................. 386/200–234, 239–248
See application file for complete search history.

(56) References Cited

U.S. PATENT DOCUMENTS

| | | |
|---|---|---|
| 8,374,682 B2 | 2/2013 | Freeman |
| 9,046,339 B2 | 6/2015 | Blatter |
| (Continued) | | |

OTHER PUBLICATIONS

Gardner, M.R. et al., "Design Considerations for Murine Retinal Imaging Using Scattering Angle Resolved Optical Coherence Tomography," Applied Science, 2018, 8, 2159 (20 pages).
(Continued)

*Primary Examiner* — Hung Q Dang
(74) *Attorney, Agent, or Firm* — Nixon Peabody LLP

(57) ABSTRACT

A method includes generating spectral image data reproducible as one or more spectral images of a plurality of regions of interest in a sample. The method also includes analyzing the spectral image data to identify a plurality of scattering components in the spectral image data, each of the plurality of scattering components being associated with one or more biological properties of the sample. The method also includes identifying a feature of interest in the sample based at least in part on one or more the identified plurality of scattering components.

9 Claims, 22 Drawing Sheets

Related U.S. Application Data

(60) Provisional application No. 62/884,508, filed on Aug. 8, 2019, provisional application No. 63/001,861, filed on Mar. 30, 2020.

(56) References Cited

U.S. PATENT DOCUMENTS

| | | | |
|---|---|---|---|
| 9,289,622 B2 | 3/2016 | Feng | |
| 2003/0225321 A1* | 12/2003 | Cote | G01N 21/21 600/318 |
| 2004/0063216 A1 | 4/2004 | Lubocki | |
| 2004/0116969 A1 | 6/2004 | Owen | |
| 2005/0122476 A1* | 6/2005 | Suzuki | A61B 3/024 351/222 |
| 2007/0252951 A1 | 11/2007 | Hammer | |
| 2008/0292151 A1 | 11/2008 | Kurtz | |
| 2009/0275841 A1 | 11/2009 | Melendez | |
| 2010/0056928 A1 | 3/2010 | Zuzak | |
| 2011/0090325 A1 | 4/2011 | Hauger | |
| 2012/0150029 A1 | 6/2012 | Debuc | |
| 2012/0165799 A1 | 6/2012 | Yamamoto | |
| 2012/0218517 A1 | 8/2012 | Imamura | |
| 2013/0109941 A1 | 5/2013 | Li | |
| 2013/0216025 A1 | 8/2013 | Chan | |
| 2013/0274610 A1 | 10/2013 | Kamshilin | |
| 2014/0160434 A1 | 6/2014 | Brown, Jr. | |
| 2014/0273858 A1 | 9/2014 | Panther | |
| 2014/0288418 A1 | 9/2014 | Milner | |
| 2014/0333898 A1* | 11/2014 | Boate | A61B 3/12 351/221 |
| 2015/0103355 A1 | 4/2015 | Bower | |
| 2015/0265150 A1 | 9/2015 | Darty | |
| 2015/0285685 A1 | 10/2015 | Wax | |
| 2016/0146723 A1 | 5/2016 | Chiba | |
| 2016/0262626 A1 | 9/2016 | Pelosi | |
| 2016/0292854 A1 | 10/2016 | Beck | |
| 2016/0331227 A1 | 11/2016 | Fingler | |
| 2017/0303787 A1 | 10/2017 | Lien | |
| 2017/0360294 A1 | 12/2017 | Satake | |
| 2018/0256025 A1 | 9/2018 | Yi | |
| 2018/0271362 A1* | 9/2018 | Palczewski | A61B 3/063 |
| 2019/0107439 A1* | 4/2019 | Vince | G01J 3/2803 |
| 2019/0204577 A1 | 7/2019 | Faris | |

OTHER PUBLICATIONS

Bissig et al., "Optical coherence tomography reveals light-dependent retinal responses in Alzheimer's disease," NeuroImage vol. 219, 117022, Jun. 5, 2020 (16 pages).

Camino et al., "Evaluation of artifact reduction in optical coherence tomography angiography with real-time tracking and motion correction technology," Biomedical Optics Express, vol. 7, No. 10, 3905, Oct. 1, 2016 (11 pages).

Gardner et al., "Scattering Angle Resolved Optical Coherence Tomography Detects Early Changes in 3xTg Alzheimer's Disease Mouse Model," Trans Vis Scit Tech., 2020;9(5):18, Apr. 24, 2020 (14 pages).

Song et al., "Multimodal Coherent Imaging of Retinal Biomarkers of Alzheimer's Disease in a Model Model," Scientific Reports, 10:7912, May 13, 2020 (11 pages).

Wei et al., "High-resolution wide-field OCT angiography with a self-navigation method to correct microsaccades and blinks," Biomedical Optics Express, vol. 11, No. 6, 3234, May 21, 2020 (12 pages).

Zang et al. "Automated motion correction using parallel-strip regirstration for wide-field en face OCT angiogram," Biomedical Optics Express, vol. 7, No. 7, 2823, Jun. 27, 2016 (14 pages).

International Search Report and Written Opinion in International Patent Application No. PCT/US2020/45044, dated Dec. 31, 2020 (17 pages).

* cited by examiner

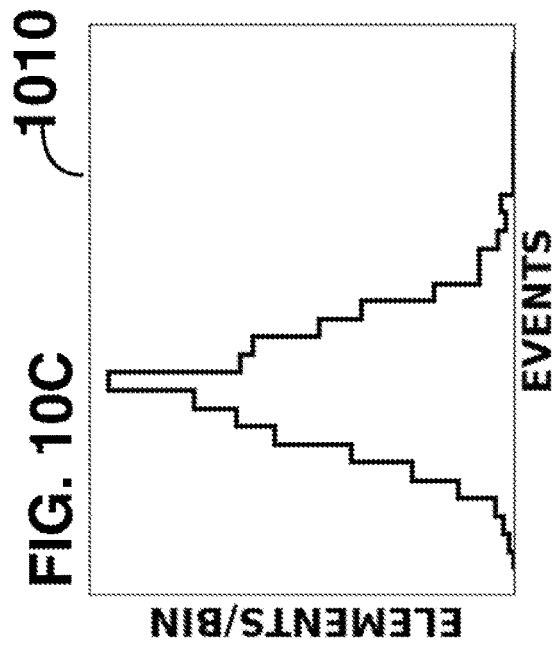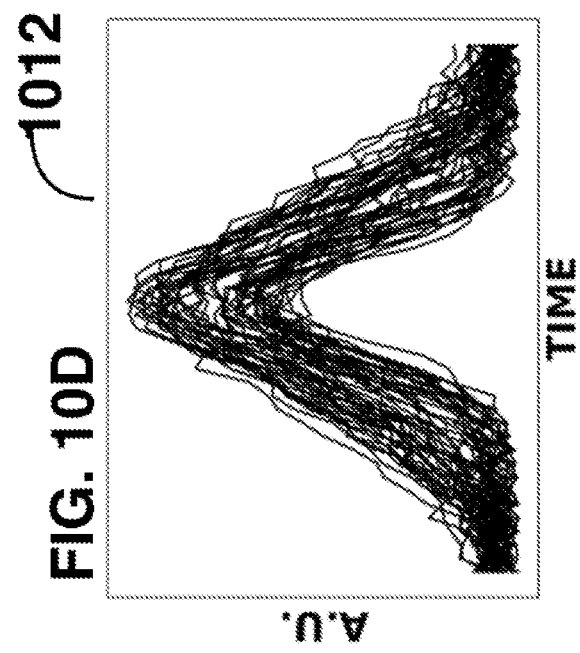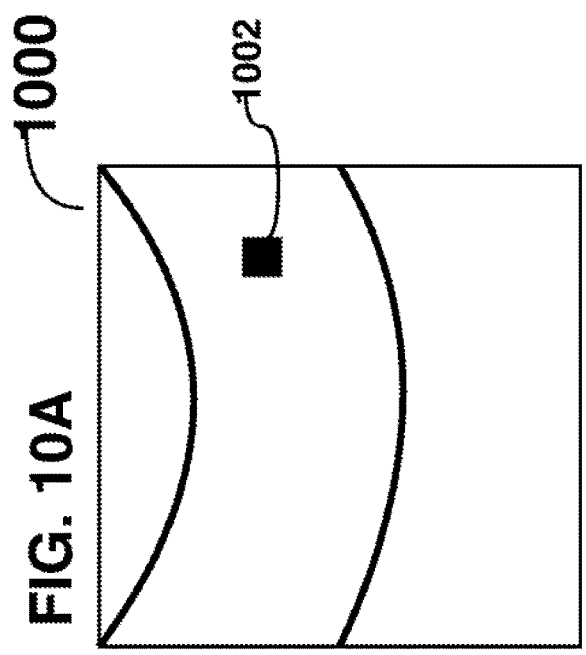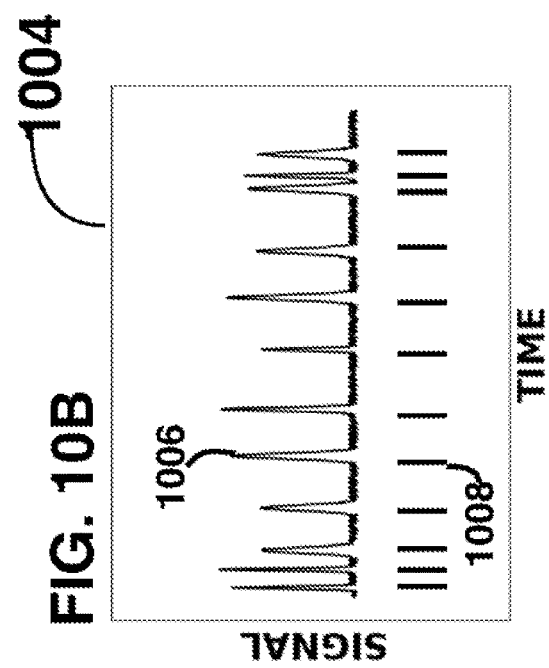

SYSTEMS AND METHODS FOR IMAGING DISEASE BIOMARKERS

CROSS REFERENCE TO RELATED APPLICATIONS

This application is a continuation of U.S. patent application Ser. No. 16/986,097, filed Aug. 5, 2020, now allowed, which claims the benefit of, and priority to, U.S. Provisional Application No. 62/884,508, filed on Aug. 8, 2019, and U.S. Provisional Application No. 63/001,861, filed on Mar. 30, 2020, each of which is hereby incorporated by reference herein in its entirety.

TECHNICAL FIELD

The present disclosure relates generally to systems and methods to identify, via imaging, features associated with disease, and more specifically, to systems and methods to obtain, via imaging, features associated disease within the eye of a living human being.

BACKGROUND

Diagnosing disease with high specificity involves identifying features (e.g. biomarkers) associated with disease-specific phenotypes. To this end, the optical accessibility of the retina makes it an attractive target within which to probe, via imaging, for features associated with disease. However, since retinal dysfunction and/or degeneration manifests itself across a broad spectrum of disease, the task of revealing features associated with disease-specific phenotypes via retinal imaging is not always straightforward. For example, certain features, such as vascular alterations, can present themselves in a multitude of diseases. This apparent lack of specificity complicates the utility of ophthalmic imaging to effectively diagnose diseases that extend beyond the eye but include ophthalmic manifestations (e.g. Alzheimer's disease).

To navigate this stumbling block, and effectively diagnose neurodegenerative disease and/or systemic pathology via ophthalmic imaging, features associated with disease-specific phenotypes must be saliently revealed. Prior efforts have been undertaken to reveal such features. For example, the use of hyperspectral imaging has been demonstrated as a promising means of detecting pathological amyloid deposition in the retina, a feature indicative of Alzheimer's disease. Additionally, metabolic imaging techniques have been employed to image retinal oxygen consumption in the context of neurodegenerative disease and diabetes. These techniques, however, lack diagnostic efficacy on the grounds that they fail to yield features indicative of disease-specific phenotypes. The systems and methods disclosed herein provide a novel route to the above-stated goal: identifying, via imaging, features indicative of diseases-specific phenotypes. The present disclosure is directed to solving these and other problems.

SUMMARY

According to some implementations of the present disclosure, a method includes generating spectral image data reproducible as one or more spectral images of a plurality of regions of interest in a sample. The method also includes analyzing the spectral image data to identify a plurality of scattering components in the spectral image data, each of the plurality of scattering components being associated with one or more biological properties of the sample. The method also includes identifying a feature of interest in the sample based at least in part on one or more the identified plurality of scattering components.

According to some implementations of the present disclosure, a system includes a light source, an imaging sensor, one or more sensors, one or more memory devices, and a control system. The light source is configured to emit light within a predetermined range of wavelengths. The imaging sensor is configured to generate spectral image data associated with the tissue sample. The one or more sensors configured to generate physiological data associated with the subject. The one or more memory devices store machine readable instructions. The control system includes one or more processors and is configured to execute the machine-readable instructions to cause light emitted from the light source to be directed onto the tissue sample along an optical path based at least in part on the physiological data. The control system is further configured to analyze the spectral image data generated by the imaging sensor between to determine a plurality of scattering components in the spectral image data, each of the plurality of scattering components being associated with one or more biological properties of the sample. The control system is further configured to identify one or more features of interest in the tissue sample based at least in part on one or more of the plurality of scattering components.

According to some implementations of the present disclosure, a device includes a support frame and one or more sensors. The support frame is configured to contact a portion of a head of a subject to aid in positioning an eye of the subject relative to an optical path such that light having a predetermined wavelength can be directed along the optical path onto the eye. The one or more sensors are coupled to the support frame and are configured to generate physiological data associated with a subject.

The above summary is not intended to represent each implementation or every aspect of the present disclosure. Additional features and benefits of the present disclosure are apparent from the detailed description and figures set forth below.

BRIEF DESCRIPTION OF THE DRAWINGS

FIG. 10A illustrates an exemplary OCT B-scan, according to some implementations of the present disclosure;

FIG. 10B illustrates an exemplary small vessel signal component, according to some implementations of the present disclosure;

FIG. 10C illustrates an exemplary histogram, according to some implementations of the present disclosure;

FIG. 10D illustrates an exemplary family of normalized red blood cell transients, according to some implementations of the present disclosure;

Figure 1:
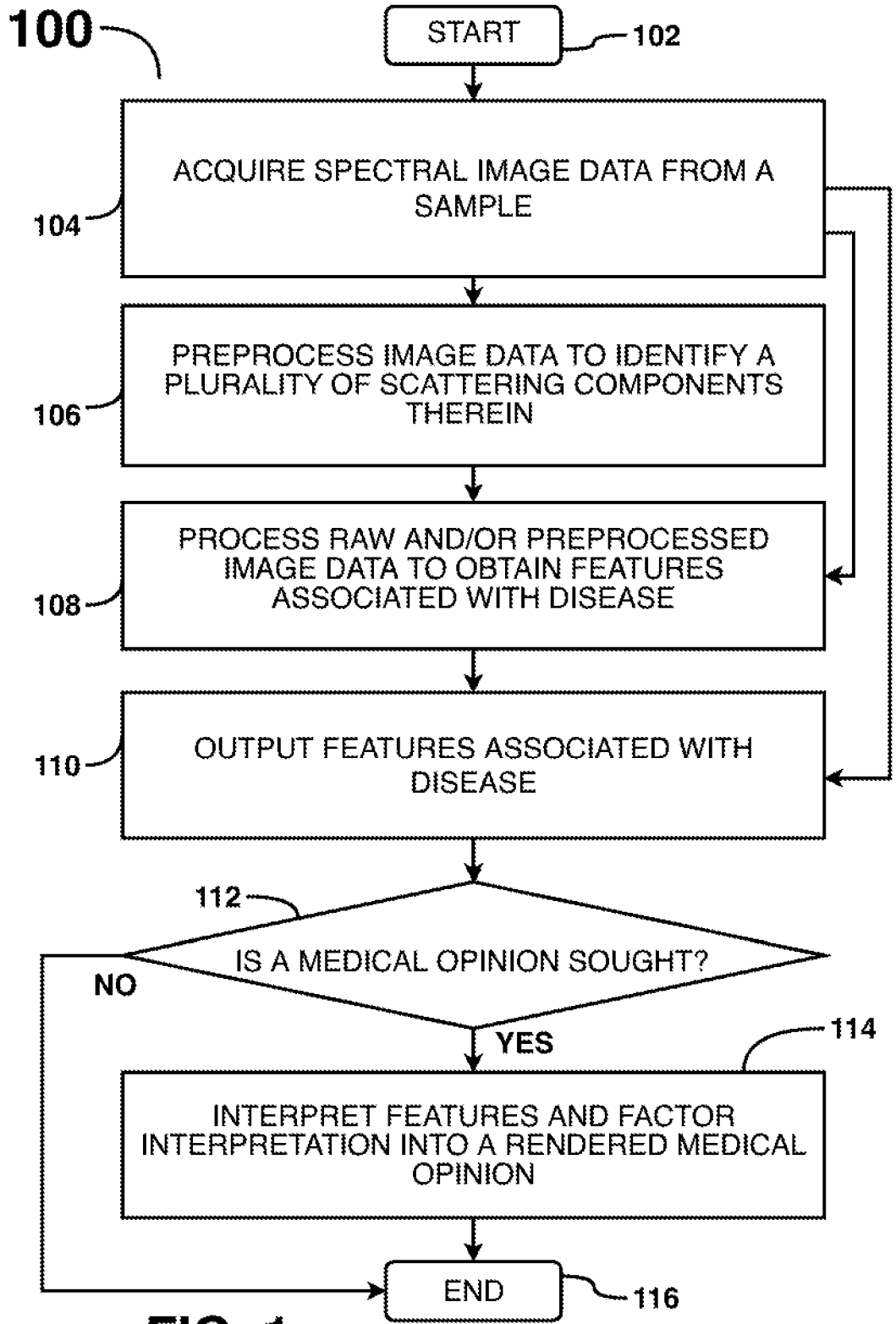
FIG. 1 is a process flow diagram for a method of acquiring, preprocessing, and processing image data to yield features associated with disease, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure provides systems and methods for acquiring, preprocessing, and/or processing image data to reveal features associated with disease. Image data is data that is, or can be transformed to be, in the form an image. To be in the form of an image, data is arranged so that at least one axis indicates a dimension of physical space. Pertaining to the acquisition of image data, systems and methods are disclosed in which: light-scattering imaging techniques are used to acquire scattering-derived image data from a biological sample; image data can preprocessed such that a plurality of scattering components can be identified therein; and, the image data can be processed to reveal features associated with disease. These features (e.g. biomarkers) may subsequently be factored into the formulation of a medical opinion, such as a diagnosis. Moreover, these features can be used to assess the efficacy of therapeutics that are likely to modify the underlying disease phenotypes.

In some implementations, the methods of the present disclosure can be performed with one or more eyes of a living human being as the imaging target or sample. As such, systems discussed herein can include ophthalmic imaging systems. In some such implementations, optical coherence tomography (OCT) systems are used. In some implementations, systems are equipped to obtain image data dynamically, at a frame-rate permitting temporally distinct scattering components to be identified. When light-scattering techniques are employed to acquire image data, the acquired image data consists of scattering components arising from biological sources that may vary predictably over space and time. This predictability can be used to provide a priori insights regarding the identification of a plurality of scattering components.

Systems and methods pertaining to the acquisition of ophthalmic image data (e.g., image data obtained from the eye) are herein disclosed, these systems and methods providing means of reducing subject burden during image acquisition. Such is accomplished via introducing at least one saccade-modulating stimulus generator into an ophthalmic imaging device, the saccade-modulating stimulus generator(s) incorporated such that the presentation of stimuli is capable of transiently modulating saccadic activity during one or more image acquisition epochs. Accompanying methods to acquire and preprocess image data in conjunction with saccade-modulating stimuli are also disclosed. These methods may involve temporally aligning image acquisition epochs relative to the presentation of saccade-modulating stimuli.

According to some implementations, methods described herein include an image acquisition process (e.g. imaging of an eye of a human) that is modified based at least in part on physiological data associated with an individual (e.g., subject) being imaged. Systems employed to execute these modifiable image acquisition processes can include one or more sensors for generating such physiological data. For example, a system can include a heart rate sensor for generating heart rate data associated with a subject. Likewise, a system can include an electroencephalographic (EEG) electrode array for generating EEG data associated with brain activity of a subject. Moreover, a system can include one or more electrooculographic (EOG) sensors for generating EOG data associated with eye movements of a subject. Further still, a system can include one or more electromyographic (EMG) sensors for generating EMG data associated with a subject. Methods involving the acquisition of physiological data alongside image data are herein provided. Also provided are methods in which physiological data provides feedback according to which image acquisition processes can be updated.

The present disclosure discusses the imaging of a sample. A sample can be a biological specimen containing one or more cells. In some implementations, the disclosed sample is a sample of ocular tissue (e.g., a cornea tissue sample, a vitreous tissue sample, a retina tissue sample, a choroidal tissue sample, a scleral tissue sample, etc.) imaged within a living human. In some other implementations, the sample may be and/or include any biological specimen. For example, a sample can be and/or include in vivo human tissue (e.g., skin (including the nailbed) tissue, brain tissue, spinal cord tissue, liver tissue, kidney tissue, colon tissue, stomach tissue, esophagus tissue, throat tissue, muscle tissue, cardiac tissue, etc., or any combination thereof). In some other implementations, a sample can be and/or include ex vivo human tissue, such as, for example, tissue obtained via biopsy and/or autopsy. In some implementations, a sample is and/or includes bodily fluids (e.g., secreted bodily fluid, and/or extracted bodily fluid such as blood). In some implementations, a sample can be in vivo or ex vivo tissue from an animal (e.g., a research animal such as a mouse, a rat, a rabbit, a guinea pig, a dog, a cat, a hamster, a non-human primate species, etc.). In some implementations, a sample can be an in vitro biological specimen that is and/or includes tissue generated from immortal cell lines, tissue generated from pluripotent stem cells, cell culture models, or any combination thereof.

The present disclosure provides systems and methods for analyzing one or more aspects and/or conditions of a subject or individual, such as, for example, a living human being. However, in some implementations, the systems and methods of the present disclosure can be used for analyzing one or more aspects and/or conditions of a research animal. The research animal can be a mouse, a rat, a rabbit, a guinea pig, a dog, a cat, a hamster, a non-human primate species, or any combination thereof.

Referring to FIG. 1, a method 100 to acquire, preprocess, and process image data obtained via spectral techniques (e.g., OCT) according to some implementations is illustrated. The acquisition, preprocessing, and processing are unified by the theme of obtaining features associated with disease. The steps constituting method 100 can be performed via manual and/or automated processes. Manual processes can include accomplishing an arbitrary task requiring direct input to a processor from a human end-user. The processor can be any suitable electronic hardware including, but not limited to, a central processing unit (CPU), a graphics processing unit (GPU), an application-specific integrated circuit (ASIC), a field-programmable gate array (FPGA), and/or a microcontroller. To provide input to a processor, a human end-user can use any and all foreseeable means of interacting with a processor. Foreseeable techniques for interacting with a processor may include, but are not limited to, the following: a mouse, a keyboard, a graphics tablet with digitizer, a touch screen device, voice recognition, and a virtual reality/augmented reality (VR/AR) environment with input sensing capabilities. Conversely, automated processes can include accomplishing an arbitrary task in which no direct input from a human end-user is required. Steps accomplished via automated means may be performed via a processor executing a set of machine executable instructions (e.g. a computer program).

Individual steps constituting the disclosed methods (e.g., the method 100) are herein described via "routines" and/or "subroutines". Routines and subroutines are defined herein as step-by-step procedures via which to accomplish one (or more) parent step(s). A routine may consist of an arbitrary number of subroutines, and these subroutines may themselves consist of an arbitrary number of subroutines. Routines and subroutines, and their constituent steps, may similarly be performed via manual and/or automated processes.

Machine executable instructions may constitute software capable of performing any and all of the steps, routines, and/or subroutines described herein. Alternatively, machine executable instructions may be embedded into application-specific hardware (e.g. an ASIC and/or FPGA) capable of performing any and all of the steps, routines, and/or subroutines described herein. Furthermore, certain steps, routines, and/or subroutines may not be explicitly defined herein, and may, for example, exist in the form of machine executable instructions. Moreover, the steps, routines, and/or subroutines described herein are agnostic with respect to whether serial and/or parallel processing techniques are employed to perform them. Furthermore, the steps, routines and/or subroutines may be performed and/or augmented by artificial intelligence (AI) and/or machine learning (ML) techniques (referred to collectively as "AWL techniques"). These AWL techniques include, but are not limited to, the following: neural networks, convolution neural networks (CNNs), deconvolution neural networks (DNNs), recurrent neural networks (RNNs; e.g. a long short-term memory (LSTM) neural network), and/or generative adversarial networks (GANs).

While the steps constituting method 100 appear in a particular order, the methods established herein are agnostic with respect to order, and may feasibly be performed in any order, such that image data can be acquired, preprocessed to identify a plurality of scattering components, and processed to obtain one or more features associated with disease. Steps belonging to routines and/or subroutines are similarly agnostic with respect to order. Moreover, one or more of the steps constituting method 100, or any steps belonging to the routines and subroutines detailed herein, may be omitted.

Method 100 is initiated by step 102, START. The subsequent step is step 104, which describes the acquisition of image data via spectral imaging techniques, for example, the acquisition of image data from the eye of a living human being via OCT. Following acquisition, image data is preprocessed such that a plurality of scattering components are identified; this is step 106. Subsequently, image data is processed to reveal features associated with disease; this is step 108. Following processing per step 108, features associated with disease are outputted; this is step 110. Following step 110, there is a decision point, step 112, at which point it is determined whether or not a medical opinion (e.g. a diagnosis and/or prognosis) shall be rendered with respect to the features outputted by step 110. If a medical opinion is not sought, the method 100 is concluded by step 116, END. Alternatively, if a medical opinion is sought, method 100 proceeds to step 112 and the features outputted via 110 are interpreted (e.g. features such as biomarkers may be assessed with respect to one or more disease specific phenotypes) to render a medical opinion. Following step 114, method 100 is concluded by step 116, END.

The acquisition of image data is performed via step 104. Central to the present disclosure is the acquisition of image data via spectral imaging techniques. In some implementations, Mie scattering theory provides principles according to which properties of biological components ("biological properties") can be imaged such that a plurality of scattering components may be identified within the acquired image data. More generally, Mie scattering theory describes how light scattering relates to the properties of objects whose physical dimensions are comparable to the wavelength(s) of incident photons. In this regard, since the physical dimensions of many biological components are comparable to the wavelengths spanned by visible and/or near-infrared light, various biological components (e.g. red blood cells) and the processes of which they are involved (e.g. blood flow) can impart scattering contributions that are spatiotemporally distinct and identifiable within image data acquired using visible and/or near-infrared light.

Visible light generally includes a band of electromagnetic radiation that includes photons of wavelengths between or equal to the lower and upper bounds of 380 and 700 nanometers, respectively. Near-infrared light generally includes a band of electromagnetic radiation that includes photons of wavelengths above 700 nanometers and less than or equal to 3000 nanometers.

Image data acquired per step 104 may be acquired via any optical imaging technique that involves acquiring image data by detecting scattered radiation at a plurality of wavelengths in the visible and/or near-infrared range, the scattered radiation scattered as a result of biological components and/or processes involving biological components. These optical imaging techniques can include, for example, OCT, scanning laser microscopy (and/or ophthalmoscopy), confocal microscopy, adaptive optics aided microscopy (and/or ophthalmoscopy), fluorescence lifetime imaging, autofluorescence imaging, multispectral imaging, hyperspectral imaging, or any combination thereof.

Figure 2:
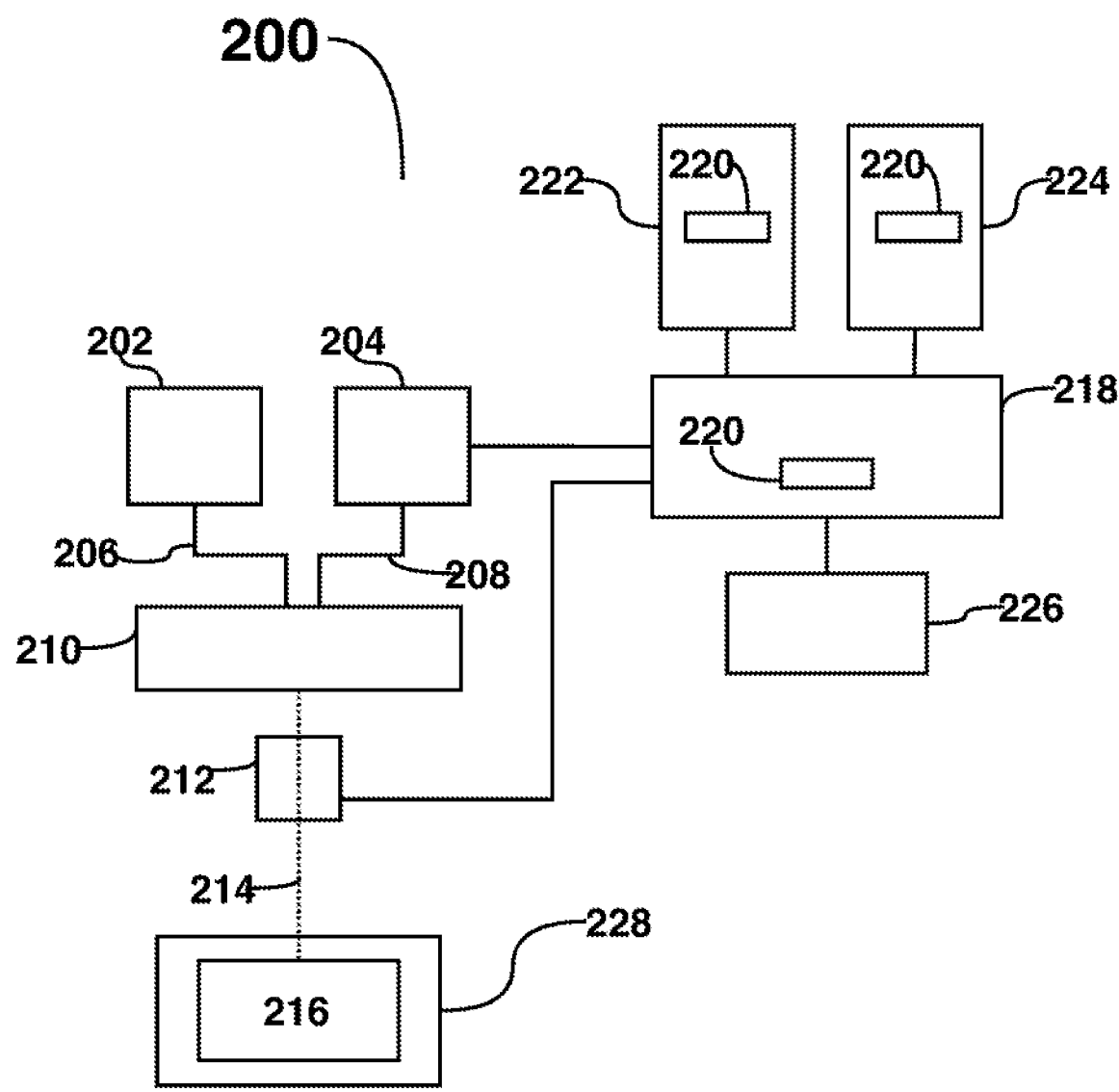
FIG. 2 is a schematic diagram of a system for implementing the method of FIG. 1, according to some implementations of the present disclosure.

An optical imaging system 200 is illustrated in FIG. 2. The system 200 includes a light source 202 capable of emitting visible and/or near infrared photons that is connected to an optics assembly 210 via an optical fiber 206. The optics assembly 210 directs incident light from the light source 202 to an optical scanning apparatus ("scanner") 212. The system 200 also includes a scanner 212, which can be connected to and controlled by a processor 218, guides an incident light beam towards one or more location(s) within and/or upon a sample 216, the sample 216 being housed, stabilized, stimulated and/or monitored by an accessory apparatus 228. In the most basic of implementations, the accessory apparatus 228 is embodied as an ophthalmic chinrest. The scanner 212 represents a steerable optical element (e.g. a galvanometer, resonant scanner, or microelectromechanical (MEMS) device) capable of scanning the sample via one or more of the following techniques: point scanning, line scanning, plane scanning, or full-field illumination (e.g. en face scanning via full-field OCT). An optical path between the optics assembly 210 and the sample 216 is shown via 214. Incident light back-scattered from the sample 216 traverses the optical path 214 back toward the optics assembly 210, where it is directed to an optical fiber 208 that connects the optics assembly 210 to a detector 204. The detector 204 is a photo-sensitive device capable of generating image data by performing one or more measurement(s) upon the light scattered from the sample 216. The detector 204 is linked to a processor 218 capable of storing, and if necessary, digitizing, the data outputted by the detector 204. Data received by the may be viewed on a graphical display 226. In some implementations, the processor 218 may indicate a plurality of processors. Additionally, the system 200 may include additional components capable of stimulating the sample.

Components of the optics assembly 210 can depend on the imaging technique(s) used to acquire image data. In general, the optics assembly 210 may comprise optical elements including, for example, one or more lenses, one or more mirrors, one or more beam splitters, one or more polarizers, one or more prisms, one or more fiber couplers, or any combination thereof. In some implementations OCT is used to acquire image data. In these implementations, the optics assembly 210 represents an interferometer containing at least two optical paths: a reference path and a sample path, the sample path including the scanner 212 and the sample 216. The reference path, however, is assumed to lie within the optics assembly 210, and is thus not shown schematized FIG. 2. The reference path(s) may be adjustable to facilitate temporal alignment of the light traveling through the sample path with light travelling through the reference path(s). Light from the reference and sample paths is recombined at or before the detector 204. When the optics assembly 210 represents an interferometer, the measurement(s) performed by the detector 204 are interferometric; that is, the measurements(s) performed by the detector 204 are based on the interference pattern(s) produced by combining light from the sample path with light from the reference path. In some implementations, a requirement of phase stability may be imposed upon the light source 202. Phase stability implies that the photons leaving a light source 202 are phase-locked with one another, thus permitting phase measurements capable of discerning sub-resolution motion.

Moreover, OCT may be implemented in one or more ways, including, but not limited to, Time-Domain OCT (TD-OCT) and Fourier-Domain OCT (FD-OCT). Implementations of OCT can also include optical coherence microscopy (OCM). Depending on the implementation, OCT can acquire image data upon which doppler, polarization-sensitive, photothermal, elastographic, functional, scattering angle, and spectroscopic measurements may be performed during and/or subsequent to the acquisition of image data. Due to faster image acquisition times and greater signal-to-noise compared with TD-OCT, implementations pertaining to FD-OCT are detailed. Implementations of FD-OCT may include Spectral Domain OCT (SD-OCT) or Swept Source OCT (SS-OCT). In implementations involving SD-OCT, the light source 202 may be embodied as a broadband light source (e.g. a superluminescent diode), and the detector 204 may be embodied as a spectrometer. In implementations involving SS-OCT, the light source 202 may be embodied as a wave-length swept light source (e.g. an ultra-short pulsed laser), and the detector 204 may be embodied as one or more photosensitive devices including photodiode, photomultiplier tube, balanced detector, or any combination thereof.

In implementations that utilize FD-OCT to acquire image data per step 104, the detector 204, regardless of how it is embodied, acquires real-valued spectral interferogram data ("raw spectrum data"). Following acquisition, the raw spectrum data acquired by the detector 204 may be prepared and/or transformed. The preparation of raw spectrum data may contain steps including, but are not limited to, the subtraction of background noise and correction for optical dispersion introduced by the sample 216 and/or other optical elements in the apparatus 200. Raw spectrum data may also be transformed to complex-valued data via inverse Fourier transform ("iFT"). The complex-valued data obtained quantifies optical properties of the sample as a function of depth; this complex-valued data is termed an axial scan or A-scan. An A-scan may be depicted as a vector of complex numbers. The elements constituting an A-scan serve to quantify sample reflectance at regularly spaced depths. Every element of this complex-valued data has two components: an amplitude and phase. The magnitude of the complex-valued data serves to quantify the intensity of scattering at a given axial depth. The phase component can provide quantitative indications indicative of spatiotemporal fluctuations at a given axial depth, and is thus of foreseeable utility when quantifying nanoscopic fluctuations undergone by subcellular scatterers. In some implementations, the process of employing an iFT to transform raw spectrum data to complex-valued data may be part of the image acquisition process, and may thus lie within the bounds of step 104. Alternatively, the process of transforming raw spectrum data may be performed subsequent to acquisition, and may thus be included in step 106.

The acquired image data contains at least one spatial dimension, or is capable of being transformed to contain at least one spatial dimension. In some implementations, acquired image data contains, or is capable of being transformed to contain, at least two spatial dimensions. OCT-based implementations involving two dimensions dictate that plurality of A-scans may be acquired to produce a two-dimensional image; a two-dimensional OCT image is referred to as a B-scan. In certain implementations, two-dimensional B-scans may be acquired in a single pass via line scanning. Some implementations involve the acquisition of image data along three dimensions. A plurality of B-scans may be acquired to produce a three-dimensional image volume; a three-dimensional OCT volume is referred to as a C-scan. In certain implementations, three dimensional image data may be acquired by employing a full-field OCT approach, in which axially adjacent en face slabs are acquired sequentially over an arbitrary depth range.

Image data acquired during step 104 contains one or more signal dimensions. A signal dimension is an axis along which image values are distributed; for example, grayscale images have one signal dimension, whereas red-green-blue (RGB) images have three. In implementations where image acquisition is performed via FD-OCT, the acquired image data exists as raw spectrum data in which values distributed along an axis corresponding to wavelength or wavenumber. Implementations of step 104 involving the transformation of raw spectrum data to complex-valued data will yield image data containing two signal dimensions: amplitude and phase. Under this arrangement, the image values are distributed on a complex plane, the amplitude corresponding to the real axis and the phase corresponding to the imaginary axis.

There exist implementations in which image data acquired via step 104 is acquired such that a plurality of scattering components are identifiable therein. Some implementations of this sort ("dynamic implementations") necessitate that the image data be acquired dynamically, at a plurality of time points, at a temporal sampling frequency sufficient to distinguish dynamic processes of interest (e.g. the flow of red blood cells through capillaries). Dynamic implementations may also involve the acquisition of image data at a sufficiently large number of time points, sufficient to distinguish statistical characteristics of speckle fluctuations. Image data acquired via dynamic implementation may be stored in a data structure consisting of one or more arrays capable of being preprocessed to construct one or more temporal signals, each temporal signal corresponding to a unique spatial image element (i.e. pixel(s) or voxel(s)).

Systems and methods capable of accomplishing step 104 are herein described. When imaging live biological specimens, sample motion can introduce artifacts into acquired image data. Artifacts of this nature are prevalent in implementations of method 100 in which ophthalmic image data is acquired. Saccadic eye movements regularly occur and can induce motion artifacts by causing the position of the imaging beam to unexpectedly change relative to the tissue being imaged. Large amplitude saccades can often be minimized by fixation upon a visual target. Prolonged fixation, however, imposes a sizable burden upon a subject undergoing an ophthalmic imaging procedure. Moreover, even during periods of fixation, fixational microsaccades (small-amplitude saccades) can persist. Pursuantly, systems and methods are disclosed in which the accessory apparatus 228 (FIG. 2) incorporates at least one saccade-modulating stimulus generator, the saccade-modulating stimulus generator(s) capable of transiently modulating the frequency and/or amplitude of saccadic eye movements. By virtue of such an arrangement, subjects are relieved of their burden to fixate upon a predominantly static target for prolonged periods.

Figure 3:
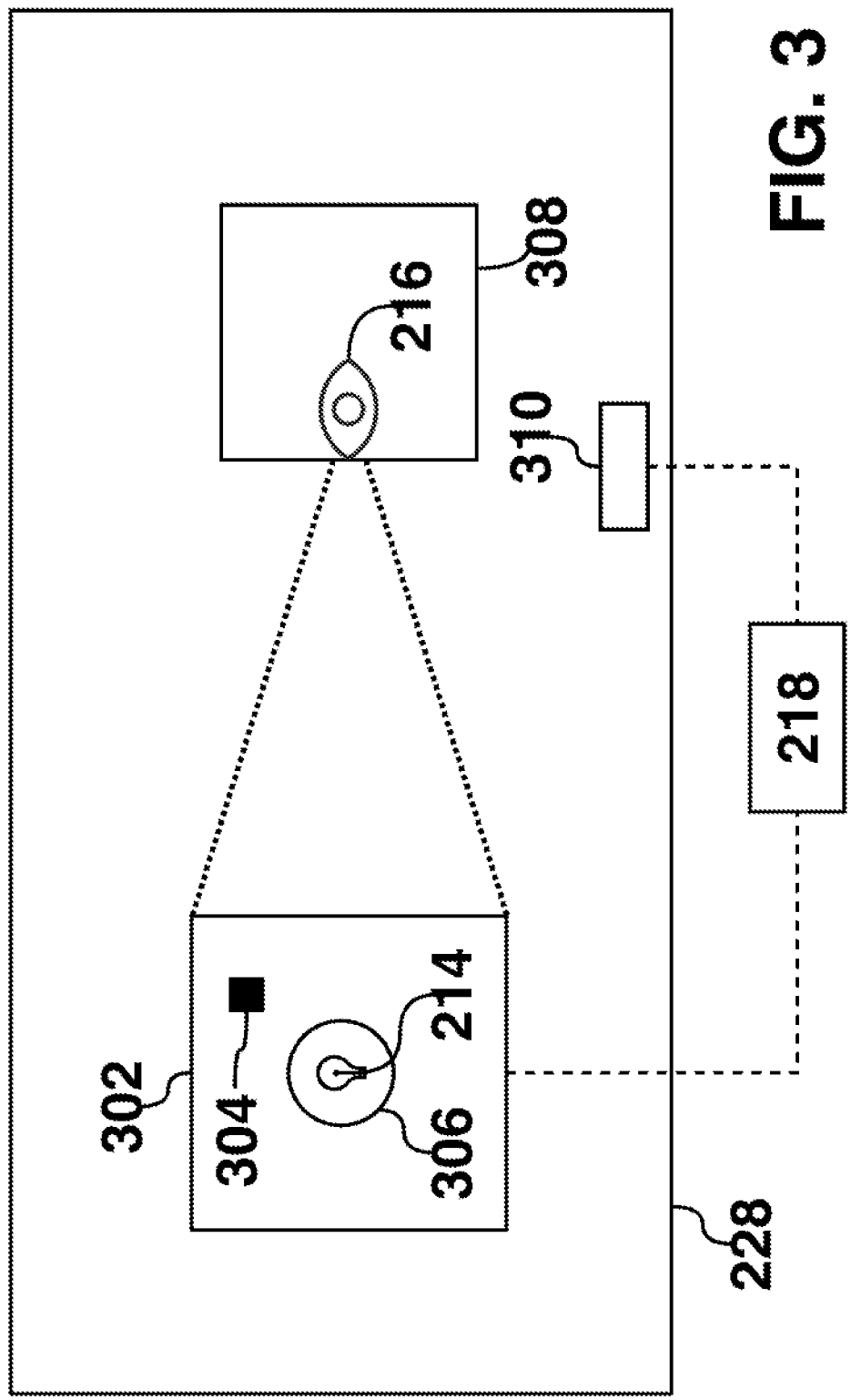
FIG. 3 is a schematic illustration of an ophthalmic imaging accessory apparatus including a saccade-modulating stimulus generator and sensors for generating physiological associated with a subject, according to some implementations of the present disclosure.

In particular implementations, systems may be described as ophthalmic imaging systems incorporating one or more saccade-modulating stimulus generators, the utility of the saccade-modulating stimulus generator(s) being that of augmenting image acquisition processes via saccadic modulation. A saccade-modulating stimulus generator is a device capable of delivering a sensory stimulus to a subject that is capable of modulating saccadic eye movements. Implementations involving the delivery of a visual stimulus, an auditory stimulus, a tactile stimulus, an electrical stimulus, or any combination thereof, are herein disclosed. In some implementations a saccade-modulating stimulus generator may deliver stimuli according to commands provided by a processor (e.g. 218). In FIG. 3, a saccade-modulating stimulus generator 302 is shown integrated into the accessory apparatus 228. In some implementations, including those shown in FIG. 3, the stimulus generator 302 is a multi-pixel visual display containing a plurality of light emitted elements 304, the light emitting elements (e.g. LEDs) capable of presenting saccade-modulating stimuli. Particular implementations feature a multi-pixel visual display 302 containing circular aperture and/or transparent region 306 through which an imaging beam 214 can be directed upon a sample; in such an arrangement a subject can direct their gaze upon a visual target that is adjacent to an imaging beam 214. Certain implementations may include a multi-pixel visual display 302 possessing the capability to display one or more visual fixation targets, the visual fixation targets capable of being relocated within pixels constituting 302. Additionally, color opponency may be employed when generating fixation and/or saccade-modulating stimuli. In particular green-purple color opponency may be advantageous, especially when imaging individuals with colorblindness. Furthermore, in some implementations the multi-pixel display 302 is capable of presenting rest stimuli during the image acquisition process, the rest stimuli being periods in which a subject can turn their attention away from the image acquisition tasks at hand. Additionally, the stimulus generator (e.g. multi-pixel display 302) may be configured to present stimuli containing one or more spatially-varying contrast patterns.

Some implementations may thus involve a multi-pixel visual display 302 capable of being toggled between one or more of the three aforementioned stimulus states: rest, fixation, and saccade-modulating. For example, the stimulus generator may be toggled between fixation and saccade-modulating stimuli, and image epochs acquired accordingly. In certain implementations, the presentation of a fixation stimulus may be taken as the presentation of a target, and the ability of an individual to fixate upon the stimulus may be taken as their ability to 'hit' the target. Accordingly, the presentation of each fixation stimulus may be viewed as a trial wherein fixation may be equated as 'success' and lack of fixation of a 'fail'. Stimuli containing one or more spatially-varying contrast patterns may be presented as saccade-moduating stimuli. When stimuli containing one more spatially-varying contrast patterns are presented as saccade-modulating stimuli, the resulting responses may be analyzed to determine features indicative of the contrast sensitivity of a subject.

Methods according to which ophthalmic image acquisition can be improved are provided. Central to these improvements are the notions of reducing subject burden, and minimizing the extent to which unwanted saccadic eye movements impart motion artifacts upon the image data during acquisition. Following the presentation of saccade-modulating stimuli, saccadic eye movements tend to become transiently modulated. This concept is leveraged to transiently inhibit microsaccades. Within epochs during which microsaccades are inhibited, a plurality of image frames (an "image epoch") can be acquired under circumstances that greatly reduce the likelihood of motion artifacts being encountered. Thus, these methods serve to improve image quality. Moreover, these methods reduce subject burden by allowing image data to be acquired within temporally interspersed epochs (i.e. image data is acquired with reduced 'duty cycle'). Under such a paradigm, prolonged fixation is not a requirement; momentary fixation is extended by transient presentation of saccade-modulating stimuli. This paradigm can be further expanded upon via implementations in which saccade-modulating stimuli is presented alongside fixation and rest stimuli.

According to some implementations, a method for modifying an image acquisition process is provided based, at least in part, on physiological data associated with a subject being imaged. In addition to acquiring image data, systems employed in these implementations include one or more sensors for generating such physiological data; such is indicated via sensors 310. When these implementations pertain to the acquisition of image data from the eye of a subject, sensors for generating physiological data can include an EEG array capable of recording physiological information streams associated with the electrical activity of a subject. Referring to FIG. 3, one or more sensors 310 (e.g., an EEG electrode array) are incorporated into (e.g., coupled to) the accessory apparatus 228. For example, the one or more sensors 310 can include an EEG electrode array that is coupled to or integrated into an ophthalmic chinrest 308 and positioned to record electrophysiological data from the forehead of a subject. Additionally, the sensors 310 can additionally or alternatively include EOG sensors, EMG sensors, heart rate sensors, pulse oximetry sensors, or any combination thereof.

Physiological data from the sensor(s) 310 is transmittable to a processor in real-time, such that physiological data can inform decision-making to optimally update parameters governing the image acquisition process. Parameters updated as a result of physiological data include whether or not to suspend (or end) an image acquisition session, the duration of image epochs to be acquired, the stimuli being presented via 302, etc. The processor 218 may likewise store the physiological data recorded by sensor(s) 310 such that the physiological data can be employed in subsequent image preprocessing, processing, and interpretation (e.g. steps 106, 108, and 114).

Figure 4:
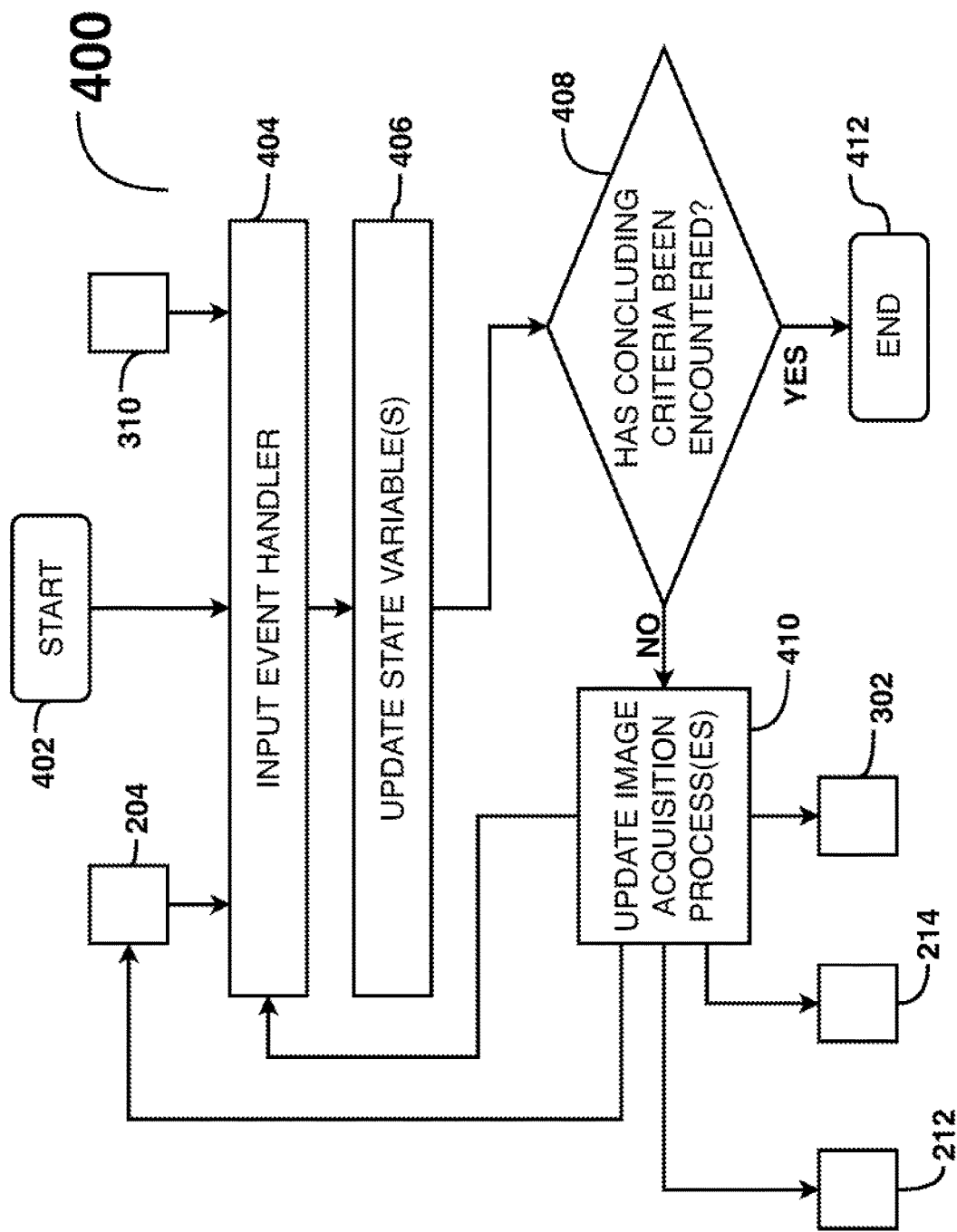
FIG. 4 is a process flow diagram for image acquisition methods, according to some implementations of the present disclosure.

Referring to FIG. 4, a method 400 for using a stimulus generator to aid in acquiring image data is illustrated. The method 400 includes sending appropriate commands to a stimulus generator 302 to control the presentation of one or more stimuli to a subject. The method 400 also includes using physiological data to modify an image acquisition process. The physiological data associated with a subject being imaged is recorded by the sensor(s) 310, received by processor 218, and thereupon used to modify an image acquisition process. Some implementations of the method 400 may employ both a saccade-modulating stimulus generator to aid, as well as the recording of physiological data to modify, an image acquisition process.

Implementations pertaining to the acquisition of ophthalmic image data are now detailed involving both recording of physiological data from, and presentation of stimuli to, an individual being imaged. The starting point is 402, via which an initiation signal is provided to 404, a command block summarizing an event handler that responds to some input. In some implementations, the event handler 404 receives external input from a detector 204 and sensors 310.

When 402 provides input to 404 a signal to begin an initialization sequence is provided to 406. As part of the initialization sequence, state variables are initialized, the state variables specifying parameters pertinent to an image acquisition process, such as parameters specifying spatiotemporal criteria according to which image data is to be acquired. According to some implementations, the method 400 may be employed to accomplish step 104. Spatiotemporal acquisition criteria include but are not limited to the following: the total number of spatial image elements over which signals are sought, the spatial range over which image data is to be acquired, the desired sampling rate at which successive frames are to be acquired, and the total number of frames sought. In addition, the initialization sequence may involve awaiting input from sensor(s) 310 that satisfies a predetermined condition indicative of subject readiness, that a subject is in a state conducive for imaging. For example, the readiness of a subject may be indicated by monitoring heart rate. In this regard, arrhythmia and/or heightened heart rate provide indications that an individual's physiological state is not conducive to imaging. Moreover, in addition to monitoring for heart rate indications, implementations may permit indications indicative of an individual's neurological state to be obtained via EEG electrode array; in these implementations, a subject's state of mental attention can be ascertained (e.g. via AWL techniques), and factored into a determination regarding the readiness of a subject. Step 406 may be iterated upon until physiological data obtained from the sensor(s) 310 indicates subject readiness.

Following update via step 406, state variables are interpreted to decide if a concluding criteria has been met; this is step 408. If so, the method 400 is concluded via END at step 412. If not, step 410 is performed, and image acquisition processes are updated via communication (e.g., data sent) to one or more of the peripherals indicated by 204, 212, 214, and 302. Additionally, step 410 can communicate updates to the input event handler 404 to initiate a subsequent iteration. In this regard, the method 400 is self-updating. According to some implementations, the event handler accepts input from a plurality of sources. In these implementations, the method 400 can include a plurality of parallel threads ("multi-threaded tasks") that are iterated in an asynchronous manner.

Figure 5:
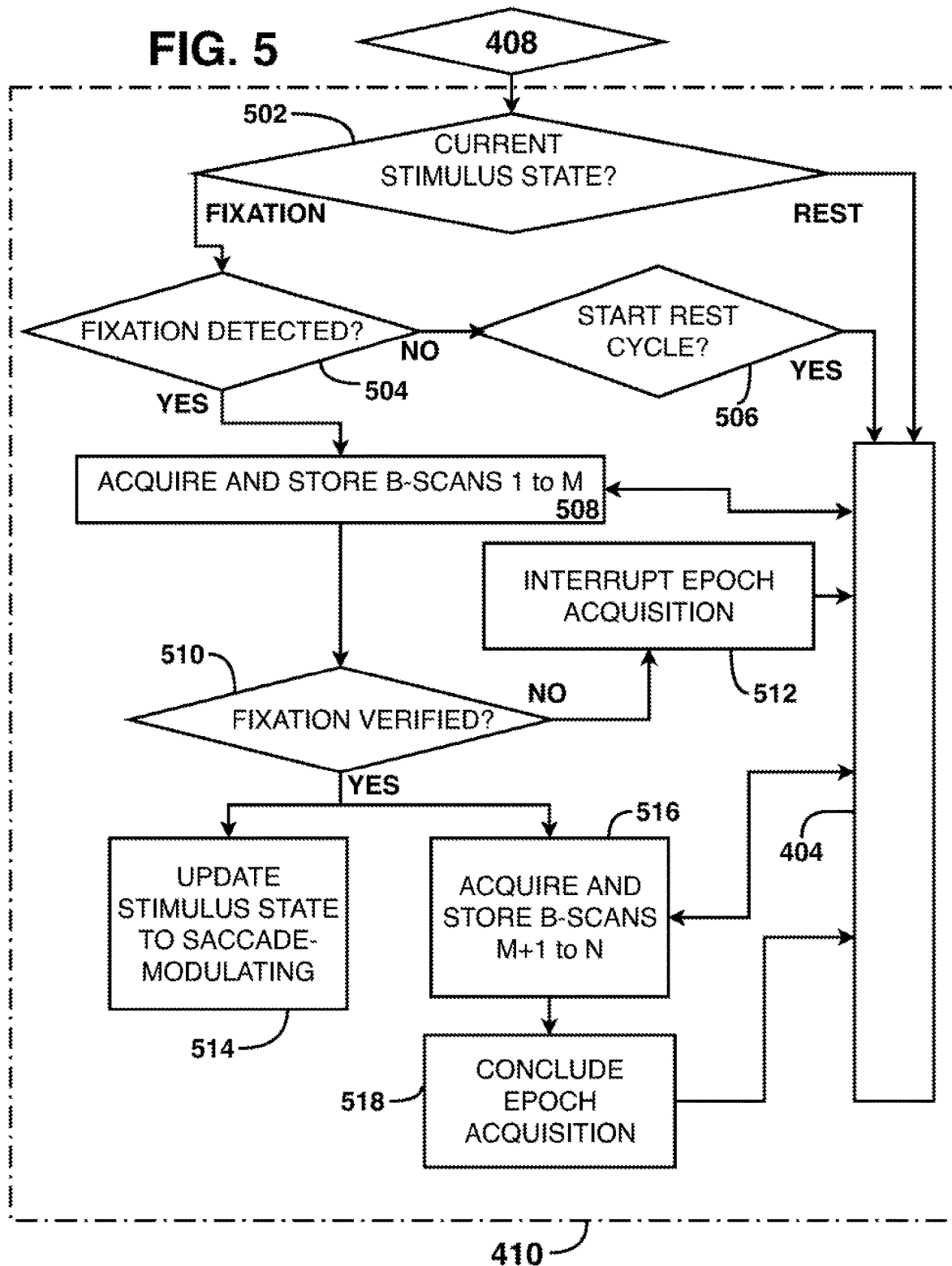
FIG. 5 is a process flow diagram for a multi-threaded image acquisition paradigm, according to some implementations of the present disclosure.

The output transmitted upon completion of step 410 is determined according to the current state variables provided by 406. Further sub-steps of step 410 are illustrated in FIG. 5, which include a collection of multi-threaded tasks, the threads capable of providing input to step 404 independently and/or asynchronously of threads to which they are parallel. Cumulatively, the implementations shown in FIG. 5 are structured around a central task: acquiring epochs of ophthalmic image data. In these implementations, the acquisition of image epochs are governed by stimuli presented by the stimulus generator 302. There are implementations in which an image epoch can consist of a sequence of stimuli such as the following: rest, fixation, saccade modulation, fixation, followed by rest. Implementations involving image epochs consisting only of saccade modulation stimuli, or epochs consisting of saccade-modulating stimuli and fixation stimuli, are also foreseeable.

Figure 6:
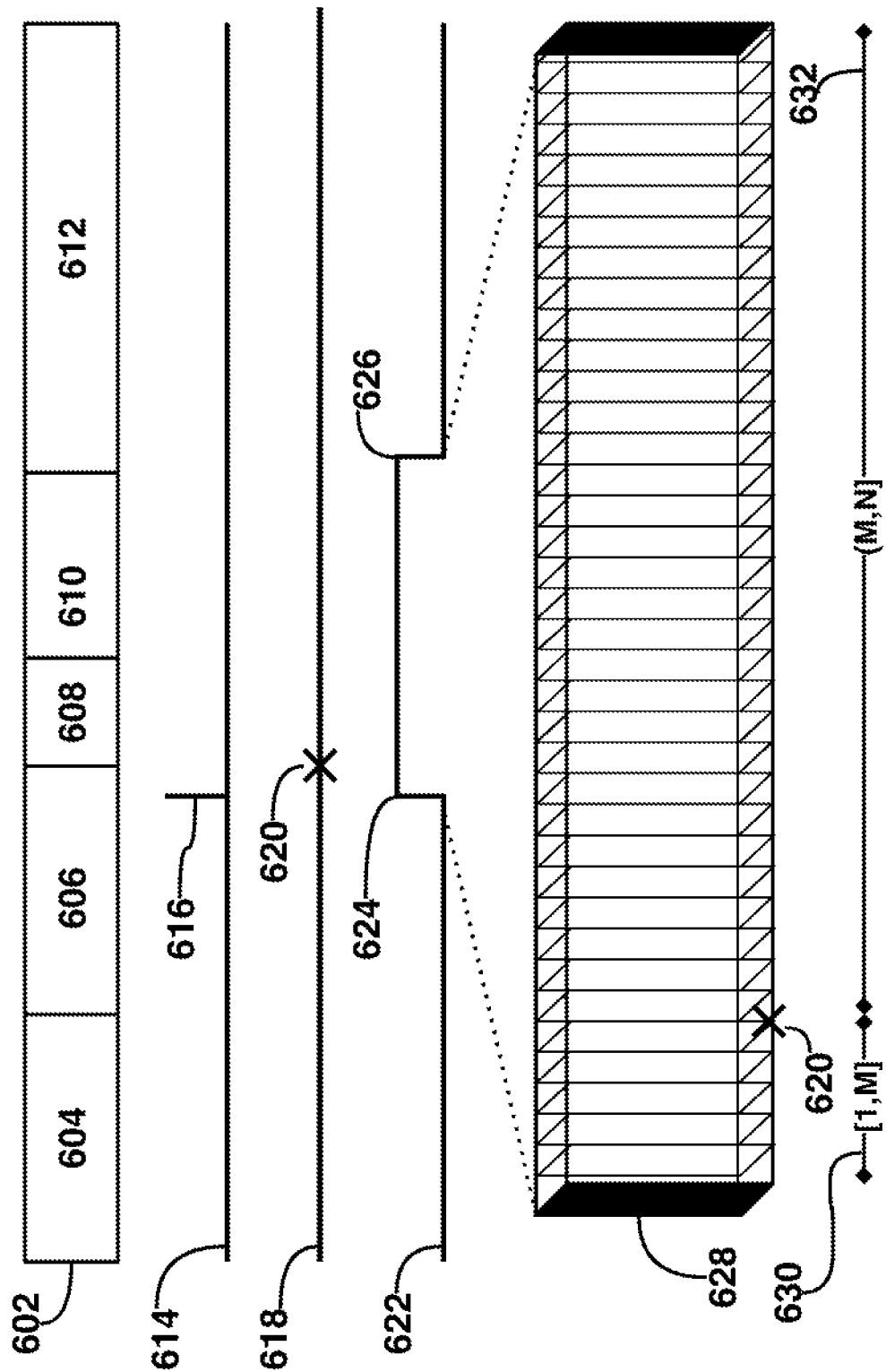
FIG. 6 illustrates an image acquisition paradigm including a presentation of a stimulus, according to some implementations of the present disclosure.

Implementations leveraging sequences of stimuli to govern the acquisition of image epochs is encapsulated in FIG. 5, the first element of which is decision point 502. At 502, a decision is made according to the current stimulus state: rest or fixation? When rest stimuli is being presented, step 410 provides a null input to 404, and does not induce a change of state variables. Such is shown in FIG. 6, which illustrates parallel streams 602, 614, 618, and 622 that combine to contribute to the acquisition of an image epoch. Sequence 602 represents the aforementioned stimuli sequence, which begins with the presentation of a rest stimulus 604. After the rest stimulus 604 has been presented for an arbitrary duration, or a change is triggered via data received from the sensor(s) 310, a fixation stimulus 606 is presented to a subject being imaged.

After the stimulus generator 302 has been toggled to provide the fixation stimulus 606, step 410 (FIG. 5) proceeds to 504, fixation detected? Decision 504 pertains to whether or not a subject is displaying indications indicative of ocular fixation with respect to the presented fixation stimulus 606. In some implementations, ocular fixation is monitored via physiological data received by the sensor(s) 310. Furthermore, these implementations may be extended to include monitoring of ocular fixation via AWL techniques in which the physiological data provides input to a trained machine learning model capable of rendering an inference predicting the likelihood that a subject is displaying indications indicative of ocular fixation. If it is determined that a subject is not displaying indications indicative of ocular fixation with respect to the presented fixation stimulus 606, step 410 proceeds to another decision point, 506, according to which it is determined whether or not to initiate a rest cycle by presenting a rest stimulus. A rest cycle is initiated in instances of subject fatigue or persistent inattention. The binary output of this decision is provided to 404 and the state variables are updated accordingly.

In FIG. 6, a thread 614 includes monitoring ocular fixation of a subject. An event 616 signifying that a subject is displaying indications indicative of ocular fixation with respect to stimulus 606 corresponds to the detection of ocular fixation. In some implementations, the detection of ocular fixation serves as the event used to initiate the acquisition of an image epoch; epochs initiated in this manner are fixation-gated. Implementations may also involve the initiation of epoch acquisition in a cardiac-gated manner. That is, a salient point in the cardiac cycle (e.g. systolic peak) is awaited and is used to initiate the acquisition of an image epoch. Additional implementations may combine fixation-gated and cardiac-gated epoch initiation; in these implementations a salient point in the cardiac cycle is awaited after fixation has been detected, with epoch acquisition being initiated thereafter.

In implementations involving OCT, an image epoch may represent a sequence of rapidly acquired B-scans, N (N being a positive integer greater than one) B-scans in length. Referring to FIG. 6, an epoch acquisition thread 622 evaluates to true between a first time 624 and a second time 626, indicating an interval over which an image epoch is to be acquired. Any and all means of acquiring a rapid succession of B-scans may herein be employed to acquire an image epoch. With respect to acquiring a rapid succession of B-scans, a thrifty acquisition paradigm may be implemented. Epochs acquired by implementing a thrifty acquisition paradigm contain two distinct sub-epochs. The first sub-epoch 508 involves the acquisition of M (M being a positive integer less than N) B-scans, and is shown in FIG. 6 as interval 630. Upon completion of sub-epoch 508 ocular fixation is verified. Some implementations may verify ocular fixation by processing two or more of the [1,M] B-scans acquired via 508. Fixation verification is represented by decision point 510, and shown in FIG. 6 is a fixation verification thread 618. The moment at which fixation verification is assessed via 510 indicated as 'X' 620. If fixation cannot be verified following acquisition of the Mth B-scan, the presently embarked upon epoch is interrupted via 512. Successful verification of fixation sends 500 to tasks 514 and 516, which results in the stimulus generator 302 being toggled from fixation 606 to saccade-modulating 608. Concurrently, B-scans M+1 through N are acquired as indicated via 516, these B-scans are graphically indicated in FIG. 6 as those in 628 bounded by interval 632.

According to certain implementations, all B-scans acquired within a given epoch will be acquired using a fixed trajectory with respect to an optical axis. These implementations can involve a scanning probe that is a dual-axis device capable of steering an imaging beam along an arbitrary trajectory; one axis, herein referred to as the Y-axis defines the linear trajectory along which A-scans are to be acquired; and a second axis, orthogonal to the first, herein referred to as the X-axis. This arrangement allows a B-scan to be acquired at an arbitrary position within an arbitrary two dimensional grid. Under this configuration, subroutines 508 and 516 require state variables specifying the following: a fixed X position at which to sweep along the Y-axis, the starting Y position, the step-size between successive A-scans, the number of A-scans to be acquired per B-scan, and the temporal sampling rate at which successive A-scans are to be acquired. Of these state variables, all except for the starting (X,Y) position are, in some implementations, set upon START 402 according to a desired spatiotemporal sampling criteria, and not updated during subsequent iterations. In these implementations, the starting X position and Y-range for a given epoch of B-scans will remain fixed for the entire duration of the given epoch. Accordingly, if the eye being imaged remains relatively stable with respect to the imaging beam, the B-scans constituting a given epoch will, ideally, be in approximate spatial alignment.

By rapidly acquiring spatially aligned B-scans, it is straightforward to acquire data in accordance with step 104 (FIG. 1). To aid in the task of acquiring B-scans that are in approximate spatial alignment, a saccade-modulating stimulus 608 seeks to modulate saccadic eye movements in an inhibitory fashion. Pursuantly, by presenting a saccade-modulating stimulus, the period of fixation that spans, at minimum, the temporal duration between the event 616 and fixation verification 620, can be transiently prolonged via presentation of 608. In some implementations, the saccade-modulating stimuli 608 is of the transient variety (e.g., about 100 ms in duration), and followed by a subsequent fixation stimulus 610, which is presented at least until the N-th B-scan has been acquired at time point 626. At this point the task of concluding image epoch acquisition 518 (FIG. 5) is performed. Per 518, the stimulus generator 302 may be toggled from fixation stimulus 610 to rest stimulus 612; at this point B-scan data constituting a complete epoch may be electronically stored for subsequent analysis. Alternatively, fixation upon fixation stimulus 610 may be awaited for, and a subsequent epoch initiated after fixation upon 610 has been detected. In this regard, 610 may become 606 for a subsequent epoch.

Implementations may involve analyzing epochs to determine if they are clean or noisy. Clean epochs are those in which a given spatial region has been sampled adequately to perform step 106 (FIG. 1), which involves preprocessing image data to identify a plurality of scattering components. To this end, implementations may require that the same spatial region of a sample 216 (e.g. retinal tissue) be predominantly present within sufficiently long spans of consecutively acquired B-scans. For example, to obtain adequate spatiotemporal sampling, the following (arbitrary criteria) may be sought: spans 100 or more B-scans in length, within which at least 95% of the B-scans therein are spatially overlapping to some extent. In some implementations, snippets of one or more consecutive B-scans lacking adequate spatiotemporal sampling can be removed from a given epoch or replaced by zeros. This is an example of data cleaning. Epochs not classified as clean are classified as noisy epochs, and are likely to have been influenced by eye movements and/or other artifacts. According to some implementations, noisy epochs may still be stored, and the data contained in all epochs, clean and noisy, can be analyzed to provide features indicative of eye movements (such as indicated by the skip connection between 104 to 110). In this sense, step 104 may involve the acquisition of image data according to which indications indicative of eye movements, and the modulation thereof, can be obtained. Moreover, by presenting saccade-modulating stimuli containing one or more spatially-varying contrast patterns, features indicative of the contrast sensitivity of a subject may be obtained.

In some implementations, it may be advantageous to acquire multiple clean epochs over approximately the same spatial region, and stitch the corresponding data together to increase signal length. It may also be advantageous to acquire image epochs at multiple spatial locations to assess different regions of a sample. Image data acquired as part of each complete epoch may be appended to an accumulator array, the accumulator array inspected followed the completion of each epoch to determine if a subsequent epoch is to be acquired. If additional epochs are to be acquired, a given spatial region may be targeted via aptly locating a fixation target and/or providing an appropriate X value at which, and Y range over which, to acquire a subsequent epoch. The sequence summarized in FIGS. 5 and 6 is then iterated through again. Alternatively, if no additional epoch is sought, the method 400 is concluded via 412 END. In implementations employing the method 400 (FIG. 4) to accomplish step 104 (FIG. 1), the conclusion of method 400 also marks the conclusion of step 104.

Referring back to FIG. 1, step 104 may include the electronic storage of data (i.e. image data, physiological data, or any combination thereof). In implementations in which OCT is employed to acquire image data, image data may be stored as raw spectrum data and/or complex-valued data. The storage of image data may be upon the processor 218, a random access memory store 222 connected to the processor 218, and/or a non-transient computer readable storage medium 224 connected to the processor 218. Machine executable instructions 220 dictating how image data is to be stored may exist as hardware and/or software, and may be contained within the processor 218, random access memory store 222, and/or non-transient computer readable medium 224. Alternatively, in certain implementations the processor 218 may export image data to an external device that is not schematized in the apparatus 200

(e.g. cloud-based storage). Following acquisition and electronic storage of image data, step 104 is taken as complete.

Step 106 is subsequently performed, and involves preprocessing data to identify a plurality of scattering components. According to the plurality of scattering contributions, features associated with disease may be obtained. In some implementations, step 106 involves the preprocessing of image data acquired from the eye(s) of a living subject, the image data containing, or capable of being transformed to contain, image elements localized within the bulk of the retina and/or upon the inner surface of the retina. Alternatively, some other implementations may involve image data localized within and/or upon the surface of the cornea.

Figure 7:
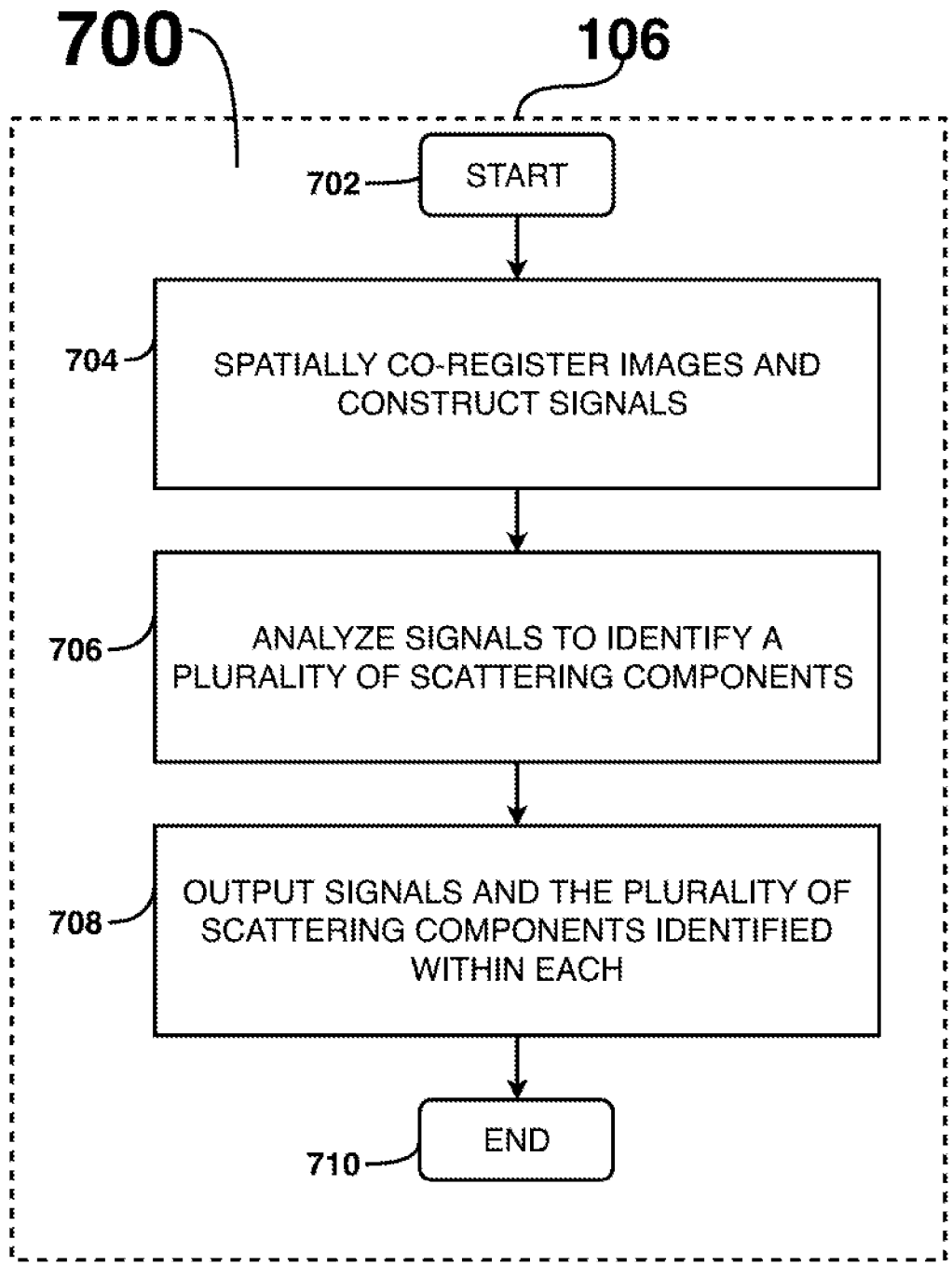
FIG. 7 is a process flow diagram for an image preprocessing method in which a plurality of images are co-registered, signals constructed, and scattering components identified therein, according to some implementations of the present disclosure.

Step 106 is detailed via flowchart in FIG. 7, which contains steps constituting a method 700 to identify a plurality of scattering components within image data. Method 700 begins with step 702, START. Via step 702, the image data acquired per step 104 is made accessible to the processor 218, or a suitable external processor capable of performing steps 702-708. In some implementations, machine executable instructions (e.g. 220) for performing steps 702-710 are contained within, or accessible by, the processor 218 (or suitable external processor). In certain implementations, the steps constituting method 700 are performed by the processor 218 in the schematized apparatus 200; all steps in method 700 will be described with respect to these implementations. Furthermore, as detailed herein, the steps constituting 700 pertain to implementations in which image data is acquired by employing an epoch-based acquisition paradigm (e.g. via employing methods such as those shown in FIG. 6). In these implementations, image data exists as an accumulator array containing data acquired during clean epochs.

For image data to be accessed by the processor 218 it is stored within the processor 218, stored within a random access memory store 222 connected to the processor 218, or stored within a non-transient computer readable medium 224 accessible to the processor 218. The image data accessible to the processor should exist in the form of an image. In implementations in which raw spectrum data generated via OCT is preprocessed, image data accessible by the processor would exist as complex-valued data or the like (e.g. an array of magnitudes corresponding to complex-valued data). Once image data in the form of an image has been made accessible to the processor 218, step 702 is taken as complete.

Figure 8A:
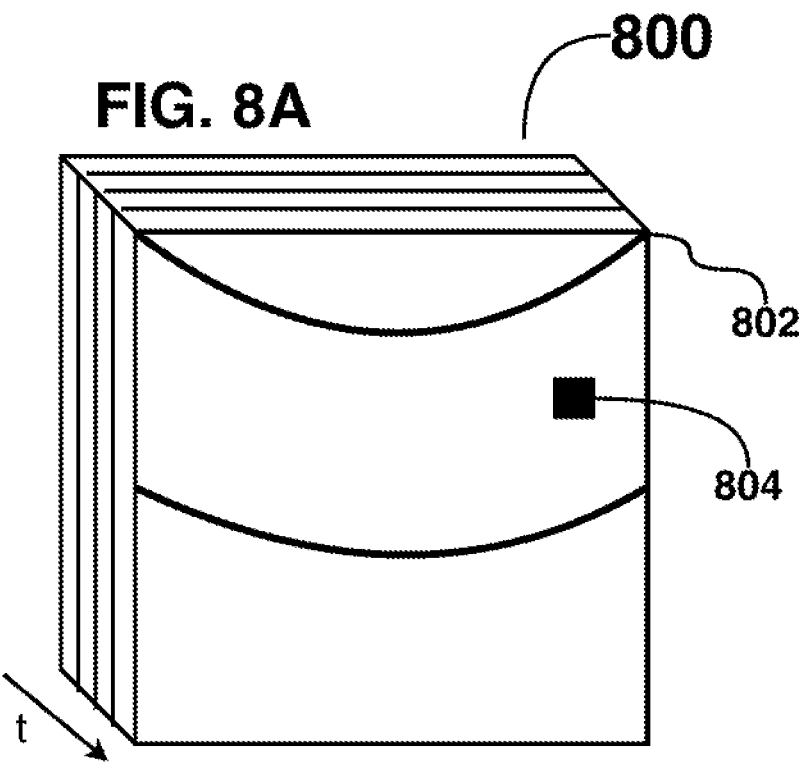
FIG. 8A illustrates a stack of co-registered epochs, according to some implementations of the present disclosure.
Figure 8B:
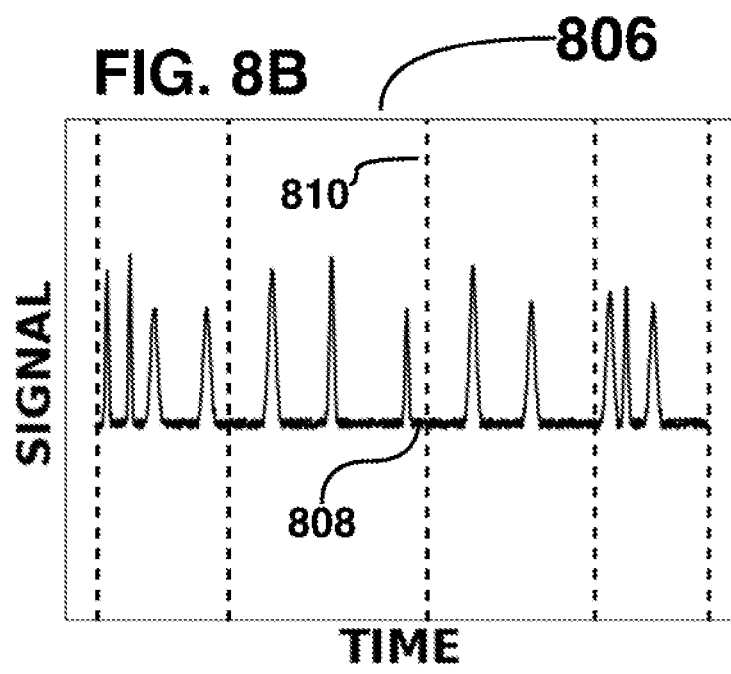
FIG. 8B illustrates a plurality of concatenated and spliced image snippets, according to some implementations of the present disclosure.

Step 704 includes co-registering the acquired image data to a uniform grid. In some implementations, step 704 is performed by sub-pixel registration methods. Co-registration allows temporal signals to be constructed such that the constructed signals correspond to one or more spatially localized image elements. In certain implementations, snippets of clean signal ("clean snippets") that correspond to approximately the same spatial image element(s) can be concatenated across one or more epochs to permit more powerful analyses. This notion is shown in FIGS. 8A and 8B. In FIG. 8A a stack of spatially co-registered epochs 800 is shown with the epochs arranged temporally. An illustrated OCT B-scan of a human retina 802 is shown, and is in spatial alignment with a plurality of B-scans across a plurality of epochs indicated within 800. A region of interest ("ROI") is indicated via 804 and is temporally traversed to reveal clean snippets. A plurality of clean snippets are shown concatenated and spliced together in FIG. 8B, which provides a plot 806 displaying a concatenated and spliced signal 808 corresponding to ROI 804; snippets from respective epochs are shown partitioned by dashed lines 810. In certain implementations, the concatenation of snippets across epochs may also involve splicing signal snippets such that they align with stimulus presentation and/or a salient feature of the cardiac cycle as recorded via sensor(s) 310. Signals such as shown that in 808 constitute the basic elements upon which the forthcoming steps in 700 operate.

Temporal signals outputted from step 704 are associated with one or more spatially localized image elements. Via step 706, these signals are analyzed to identify a plurality of scattering components. According to some implementations, the analysis of a signal may determine if the signal contains indications indicative of one or more of biological properties, or sets of biological properties, within the sample. A first set of biological properties may include large diameter blood vessels (e.g., blood vessels larger than capillaries or those having an inner diameter greater than or equal to about 20 microns) and the flow of blood cells through these large diameter blood vessels; this first set of properties is herein referred to as large vessel properties. A second set of biological properties may include small diameter blood vessels (e.g., capillary blood vessels or those having an inner diameter less than about 20 microns) and the flow of blood cells through these small diameter blood vessels; this second set of properties is herein referred to as small vessel properties. A third set of biological properties may include non-vascular tissue (e.g., tissue parenchyma); this third set of properties is herein referred to as parenchymal. The identification of a plurality of scattering components may be performed according to the aforementioned sets of biological properties to yield a first scattering component associated with large vessel properties (e.g., a large vessel scattering component), a second scattering component associated with small vessel properties (e.g., a small vessel scattering component), and a third scattering component associated with parenchymal properties (e.g., a parenchymal scattering component).

According to some implementations, the identification of a plurality of signal components via step 706 may be aided by a priori knowledge of the biological properties within the sample being imaged. For example, when the retina constitutes the sample, signals are likely to be influenced by large vessel properties, small vessel properties, and/or parenchymal properties. These a priori insights can inform the identification task at hand. Large vessel properties tend to be dominated by a nearly-continuous stream of blood cells coursing through vasculature. Small vessel properties on the other hand tend to be associated with intermittent, single-file flow of blood cells through capillaries. Parenchymal properties tend to be associated with non-vascular cells and the subcellular components thereof. More specifically, within the retina parenchymal properties may include axonal ultrastructure, synaptic ultrastructure, axonal transport, neuronal activity, immunological activity, mitochondrial motility, mitochondrial ultrastructure, or any combination thereof.

Figure 9B:
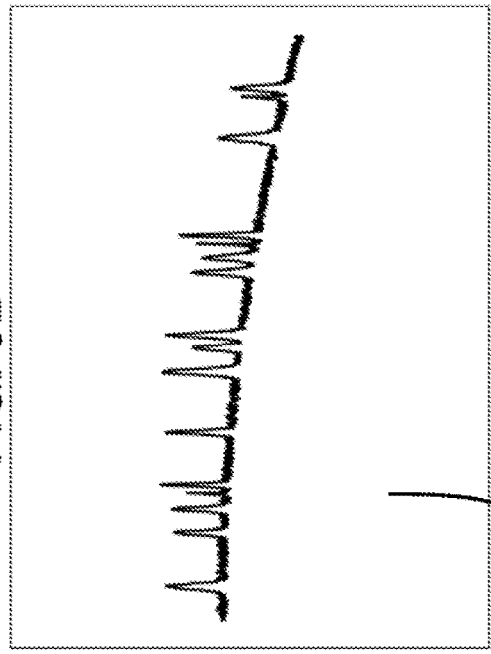
FIG. 9B illustrates an exemplary signal indicative of small vessel scattering components, according to some implementations of the present disclosure.
Figure 9D:
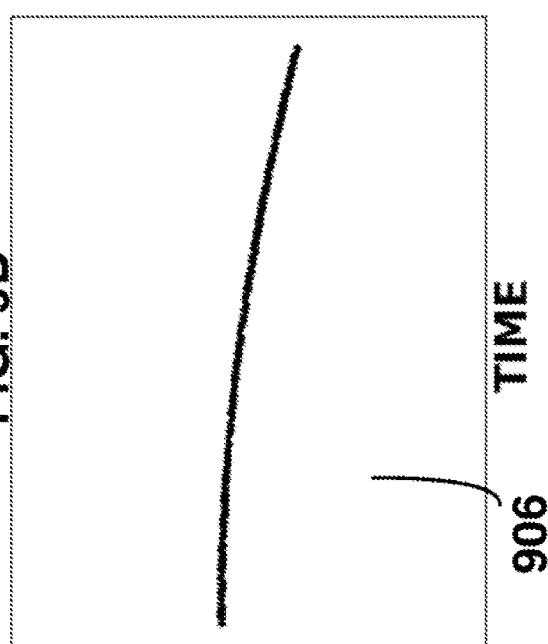
FIG. 9D illustrates a parenchymal component of the signal of FIG. 9B, according to some implementations of the present disclosure.
Figure 9A:
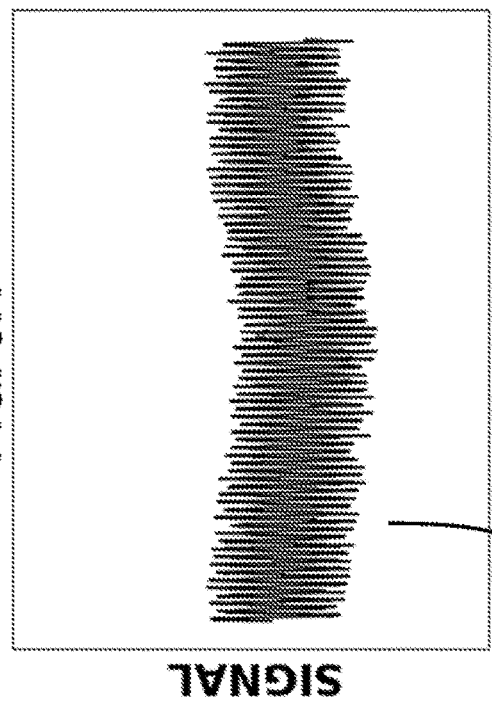
FIG. 9A illustrates an exemplary signal indicative of large vessel scattering components, according to some implementations of the present disclosure.

Of the biological properties exemplified, large vessel properties tend to be more saliently identifiable than the others. The nearly-continuous stream of blood cells indicative of large vessel properties often leads to a succession of large-amplitude signal deflections. As such, signals identified as containing an indication indicative of large vessel scattering tend to be inherently unpredictable. This can make the identification of small vessel scattering components and parenchymal scattering components difficult within signals identified as containing an indication indicative of large vessel scattering. Thus, in particular implementations, signals identified as containing an indication indicative of a large vessel scattering component are identified as consisting solely of a large vessel scattering component with the other components being identified as null (e.g. vectors of zeros); such a signal 900 is depicted in FIG. 9A. Indications indicative of a small vessel component and indications indicative of a parenchymal component can, on the other hand, be present within the same signal; such a signal 902 is depicted in FIG. 9B.

Step 706 may be further extended to separately identify the small vessel and parenchymal scattering components. This can be accomplished by leveraging a priori knowledge pertaining to small vessel properties. Through capillaries, blood cells tend to flow single file in a temporally intermittent manner. Blood flow through capillaries is thus associated with transient signal increases as blood cells pass transversely through the imaging beam. Alternatively, blood cells may stall out within capillaries. This stalling of blood cells produces a rapid signal increase followed by an elevated plateau and/or an elevated plateau followed by a rapid signal decrease. For simplicity stalled red blood cells are not elaborated upon herein. However, some implementations can, in a straightforward manner, extend the present discussion to stalled red blood cells.

Figure 9C:
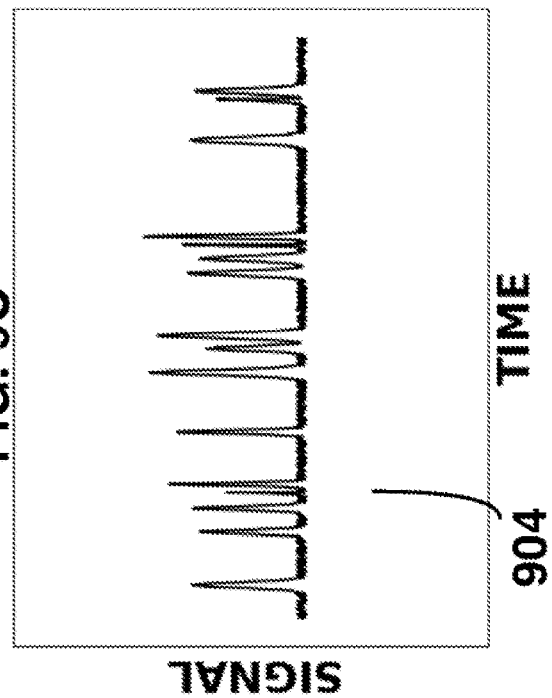
FIG. 9C illustrates a small vessel component of the signal of FIG. 9B, according to some implementations of the present disclosure.

The transient signal increases and decreases associated with the movement of blood cells through capillaries can be approximated by Gaussian curves. Thus, since small vessel scattering can be identified as attributable to the flow of blood cells through capillaries, the small vessel scattering component can be effectively distinguished from the parenchymal scattering component. This can be accomplished via convolution with a Gaussian kernel. The signal 902 in FIG. 9B, which contains indications indicative of a small vessel scattering component and a parenchymal scattering component, has been filtered accordingly. FIG. 9C illustrates a small vessel component 904 of the signal 902 (FIG. 9B). FIG. 9D illustrates a parenchymal component 906 of the signal 902 (FIG. 9B). Each Gaussian-shaped deflection contained in the small vessel component 904 is associated with the passage of an individual blood cell through a capillary segment. Parenchymal scattering, such as that shown in the parenchymal component 906, can be of the steady-state variety, and may be indicated by slow changes throughout the time course of a signal. For example, one such parenchymal property known to produce these slow changes is the osmotic swelling and/or shrinking of cells (e.g. neurons) in response to changes in activity. Alternatively, the parenchymal scattering component may contain speckle fluctuations occurring within a given signal. For example, one such parenchymal property that may be indicated by such speckle fluctuation is axonal transport.

The signals constructed via step 704 and their scattering components identified via step 706 are outputted per step 708; the signals and their respective scattering components are referred to collectively as preprocessed image data. Following output via step 708, method 700 reaches END 710. During the conclusion of method 700 the preprocessed image data may be electronically stored in a similar fashion to that described at the conclusion of step 104. Image data has thus been preprocessed in accordance with step 106. Via identifying a large vessel component and a small vessel component, the preprocessed image data outputted from 106 can be used to generate an angiogram according to which vasculature is mapped in a property-specific manner (i.e. a manner involving large vessel process and small vessel properties). Also, in certain implementations, AWL techniques may be used to accomplish step 106 and identify the plurality of scattering components described above.

Step 108 is now performed according to which image data is processed to obtain features associated with disease. In some implementations the preprocessed image data outputted at the conclusion of step 106 is processed to obtain features associated with disease. In other implementations, image data acquired per step 104, and not preprocessed by step 106 ("raw image data"; e.g. raw spectrum data), is processed to obtain features associated with disease. In additional implementations, the processing of raw image data to obtain features associated with disease is informed via preprocessed image data. The inclusion of raw image data in step 108 is indicated via the skip connection connecting steps 104 and 108. Moreover, according to these additional implementations in which FD-OCT is used to acquire raw image data, features associated with disease can be obtained by processing raw spectrum data in an informed way. Pertaining to these additional implementations, features obtained in step 108 are guided by the plurality of scattering components identified in step 106.

FIGS. 10A-D depict a corresponding implementation of step 108 in which features indicative of microvascular dysfunction may be obtained. FIG. 10A, shows an illustrated OCT B-scan 1000. The OCT B-scan 1000 includes an image element 1002 that corresponds to a signal that has been preprocessed per step 106 to identify the small vessel scattering component therein. FIG. 10B illustrates a small vessel signal component 1004 resulting from the image element 1002. Contained in the small vessel signal component 1004 are transients 1006 indicative of red blood cell flow through a capillary intersecting the corresponding image element 1002. To obtain features indicative of microvascular function, one or more computational techniques may be employed. In particular, it may be advantageous to leverage the single-file manner in which red blood cells typically flow through capillaries; each red blood cell transient (e.g., transient 1006) is due to a single cell. Such allows microvascular flow to be quantified over space and time. Foreseeable implementations allow capillary flow maps to be generated by computing the rate at which red blood cell transients are encountered in a given signal (e.g., the small vessel signal component 1004). By performing this flow rate computation over a plurality of spatially unique signals, such as those typically spanning an OCT B-scan, capillary flow maps can be generated and may overlaid upon structural and/or angiographic OCT data to graphically display features indicative of microvascular function.

The above techniques treat the flow of blood cells in a binary manner. That is, signals (e.g., the small vessel signal component 1004) are in essence reduced to sparse Boolean vectors; such is shown via raster ticks 1008 (FIG. 10B). This class of methods, in which blood cell passage is treated as a binary event, lends itself to Poisson analysis. For example, image elements of interest within a ROI (e.g. a specific retinal layer) can be aggregated into a histogram according to the rate at which blood cell transients are detected therein. FIG. 10C illustrates an exemplary histogram 1010. The resulting histogram 1010 can be modeled as a Poisson distribution, and the metrics stemming from this modeling interpreted to obtain features indicative of microvascular function.

Non-binary techniques for obtaining features indicative of microvascular function in which the passage of red blood cells is not reduced to a Boolean vector may also be employed in some implementations of step 108. These non-binary techniques are leveraged to assess blood cell dynamics at the level of single cells. As mentioned, the flow of blood cells can be modeled via a Gaussian function. FIG.

10D illustrates a family of normalized red blood cell transients 1012 in which inter-event variability is observable. This variability may be quantified to yield features indicative of microvascular function. For example, consider a case in which the family of transients shown in the histogram 1010 corresponds to events observed in a single capillary segment. By analyzing the variability between individual red blood cell transients, features associated with blood cell dynamics can be obtained as a foreseeable means of accomplishing step 108.

Processing described according to FIGS. 10A-10D employs only preprocessed image data outputted from 106 to accomplish step 108. Other implementations use the preprocessed image data to inform processing of raw image data (e.g. raw spectrum data). According to these implementations, spectroscopic processing may be informed by scattering components identified via step 106. In some of these implementations, especially those in which OCT was used to acquire raw spectrum data, spectroscopic processing can be focused upon windows of time during which the flow of individual blood cells is assumed to be influencing the acquired raw spectra. That is, the preprocessed signals yielded by 106 are used to identify raw spectra that may be influenced by the flow of individual blood cells. Once identified in this manner, the corresponding raw spectra are processed spectroscopically to yield features indicative of microvascular function. In particular, implementations of this sort can yield features indicative of the shape of individual red blood cells as they pass through capillaries. While passing through capillaries, red blood cells commonly flow in two ways: by acting as a rigid disk and spinning as a wheel, or tumbling (e.g. tumbling in folded conformation as a means of passing through constricted capillaries). The geometry inherent to each mechanism of flow is distinct, which in turn, by virtue of Mie scattering principles, is likely to result in distinct spectroscopic signatures when imaging is performed in the spectral domain (e.g. FD-OCT). Such implementations are extensions of spectroscopic OCT to assessment of capillary-level hemodynamics. Accordingly, a method is presented in which spectroscopic OCT is employed to discern rolling from tumbling and/or folded red blood cells.

Spectroscopic processing of raw spectrum data leverages the notion that oscillations or other features present in the raw spectra are indicative of scatterer geometry (e.g. spherical or cylindrical) and/or spatial orientation (e.g. transverse or axial). Accordingly, by temporally windowing spectroscopic processing in such a way that raw spectra are identified as likely to be influenced by the flow of individual blood cells, it is possible to spectroscopically assess red blood cells as they flow through capillaries. In particular, blood cell transients (e.g. those shown in 1012 in FIG. 10D) may span spectra acquired at multiple time points. In this regard, the spectral influence of a given red blood cell can be observed at multiple points of time, the number of points corresponding to the width of the transient to which the given red blood cell is associated.

The manner in which red blood cells influence raw spectra depends on their geometry and their orientation with respect to the imaging beam incident upon the sample. When rolling, red blood cells adopt a morphology akin to a rigid disk, and are thus unlikely to undergo rapid changes of orientation during the time over which their corresponding transients are observed. Tumbling, potentially folded, red blood cells present a different case entirely, tending to undergo incessant changes of orientation with respect to the incident imaging beam. Therefore, the spectra associated with rolling red blood cells are expected to be much less variable than the spectra associated with tumbling red blood cells. To capture imaging features of this sort, an extension of spectroscopic OCT, herein referred to as spectral variance analysis, is introduced. Spectral variance analysis investigates how the spectra associated with one or more image elements of interest change as a function of time.

Figure 11:
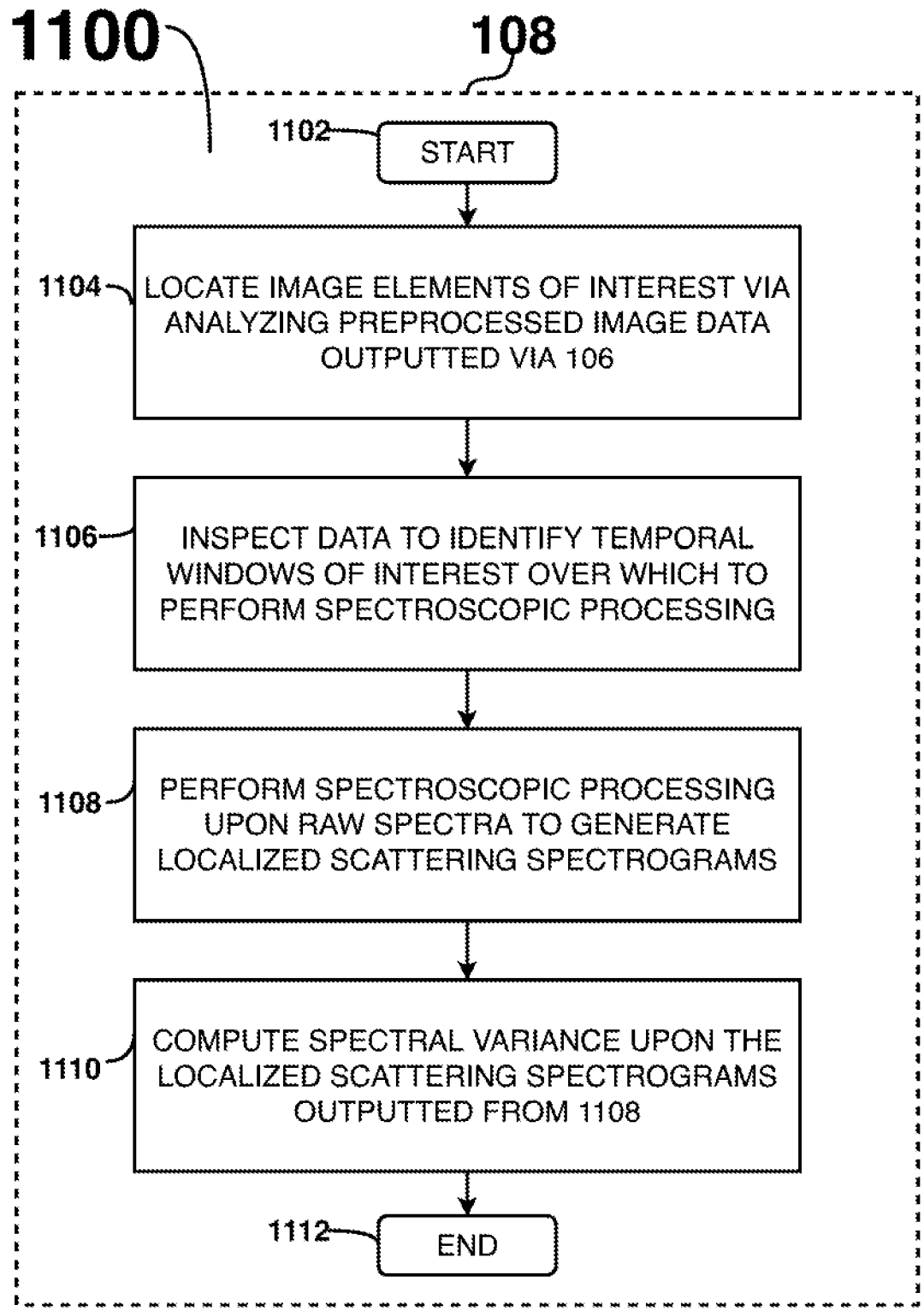
FIG. 11 is a process flow diagram for spectral variance analysis methods, according to some implementations of the present disclosure.

Referring to FIG. 11, a method 1100 of spectral variance analysis for use with the method 100 (FIG. 1) is shown. Method 1100 begins with START 1102; within step 1102 the preprocessed data outputted from 106 as well as the raw spectrum data acquired during 104 are available to a processor. Next, step 1104 is performed which involves locating image elements of interest via analyzing the preprocessed image data outputted by step 106. In implementations of spectral variance analysis in which the dynamics of red blood cells provide desired output, step 1104 involves locating according to their small vessel component. Subsequently, via step 1106, one or more temporal windows over which to perform spectral variance analysis are identified. These temporal windows may, for example, be identified by finding windows spanning the full-width half-maximum regions of blood cell transients. With spatial image elements located, and temporal windows befitting spectral variance analysis identified, step 1108 is performed.

Step 1108 includes spectroscopically processing the raw spectra corresponding to image elements located via step 1104 over temporal windows identified via step 1106. The raw spectra acquired via step 104 correspond to the entire range of depth of an A-scan; the raw spectra can thus be viewed as delocalized scattering spectra. Step 1108 involves processing these raw spectra to obtain spatially localized scattering spectra. This aspect of step 1108 may employ the use of the short-time Fourier transform (STFT) to yield localized scattering spectra corresponding to image elements of interest. By applying step 1108 (e.g. employing a STFT) over temporal windows spanning multiple raw spectra, a plurality of localized scattering spectra ("spectrograms") corresponding to individual image element(s) can then be analyzed such that the variance within and/or between spectrograms can be computed; this is the essence of step 1110.

Computation of spectral variance within such spectrograms is now described. Variance within a spectrogram may be computed by averaging all spectrums in a given spectrogram and then computing how each spectrum in the spectrogram differs from the average spectrum; this is computation of variance in the general (i.e. feature agnostic) sense. Prior to averaging, the spectrums may be normalized and/or weighted. Computation of variance may also be performed with respect to various features in the spectra. For example, spectral variance may be computed with respect to the shape of spectra within a given spectrogram. Computation of variance with respect to spectral shape may be accomplished by normalizing the spectra and thereafter computing variance as described above in the feature agnostic case. Following normalization, variance with respect to the shape of spectra can be obtained by using auto- and/or cross-correlation methods, as well as other suitable techniques not mentioned herein. Moreover, spectral variance may be computed with respect to the scale of spectra within a given spectrogram. It may be advantageous to investigate scale variance only in spectrograms that have considerably low shape variance. Spectral scale variance computed in this manner is thus a two-part process involving first verifying that the spectra in a given spectrogram display low shape variance, and thereafter computing variance upon the unnormalized spectra as described above in the feature agnostic case.

Figure 12A:
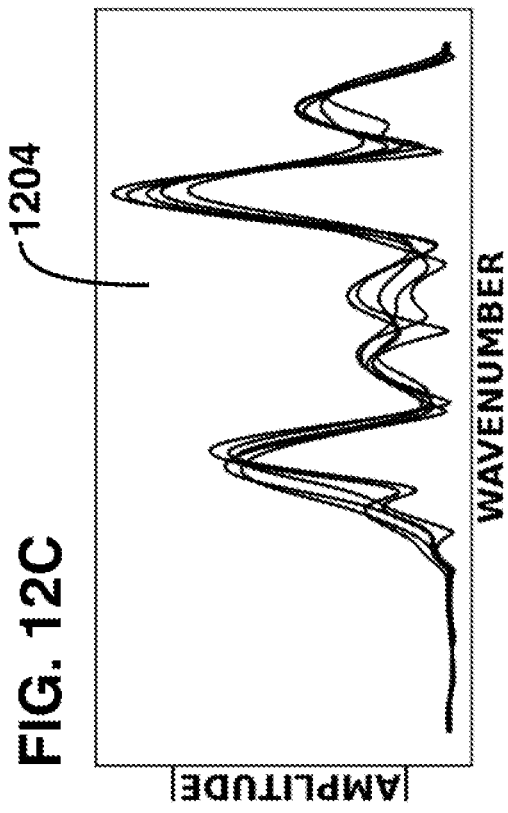
FIG. 12A illustrates a first spectrogram, according to some implementations of the present disclosure.
Figure 12B:
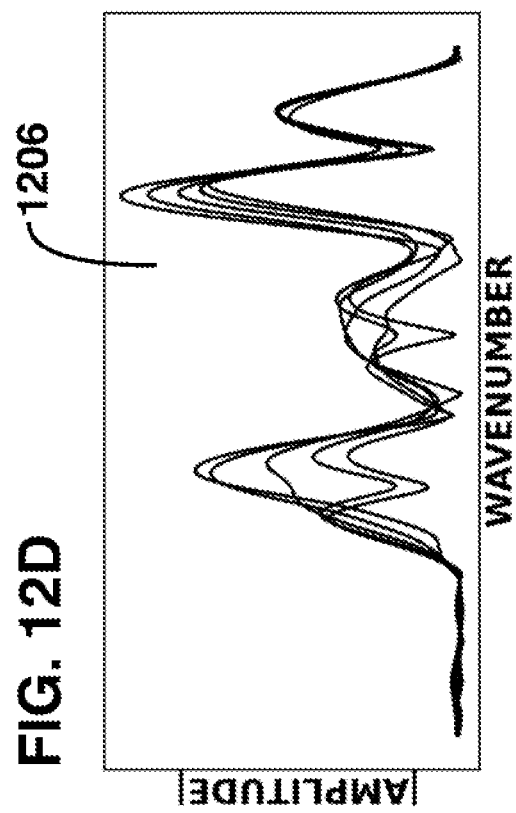
FIG. 12B illustrates a second spectrogram, according to some implementations of the present disclosure.

Spectrograms of localized scattering spectra corresponding to two different image elements are shown via FIGS. 12A-12B, a first spectrogram 1200 and a second spectrogram 1202, respectively. The spectra in the first and second spectrograms 1200 and 1202 each span a window of time identified as a red blood cell transient. Thus, by computing the variance within the first and second spectrograms 1200 and 1202, features indicative of microvascular function can be obtained. To this end, it may be advantageous to compute variance with respect to spectra shape. Along these lines, the shapes of spectra in the first spectrogram 1200 vary minimally; computation of spectral shape variance is thus expected to yield a low value that can be interpreted as an indication indicative of rolling red blood cell dynamics. Alternatively, the shapes of spectra in the second spectrogram 1202 vary considerably; computation of spectral shape variance in this instance is thus expected to yield a high value that can be interpreted as an indication indicative of tumbling red blood cell dynamics Spectral variances are computed via step 1110 and thereafter method 1100 reaches END 1112. Endpoint 1112 can likewise mark the termination of step 108 of the method 100 (FIG. 1). In the context of step 108, spectral variance based features can be indicative of microvascular function; higher than normal incidence of tumbling red blood cells, as determined by spectral variance methods 1100, can be interpreted as a feature associated with disease.

Features indicative of parenchymal function can also be obtained via spectral variance methods (e.g., the method 1100). According to these implementations, step 1104 involves utilizing the parenchymal scattering component outputted via 106 to local parenchymal elements of interest. Likewise, step 1106 may involve determining temporal windows over which to assess parenchymal function. In particular, these temporal windows can span one or more epochs and define windows of time over which to probe for changes in the distribution of scatterers. In these instances, spectral variance methods may yield features indicative of parenchymal function, such features including but not limited to axonal transport. Moreover, as localized scattering spectra obtained via 1108 can be processed to yield metrics indicative of scatterer size within a given image element, spectral variance methods may be extended to provide features indicative of axonal transport in a cargo-specific manner (e.g. features indicative of mitochondrial motility).

Features indicative of parenchymal function may also include features indicative of neuronal activity. Neuronal activity is associated with osmotic undulations of cell volume. These osmotic undulations of cell volume impart optical changes within the sample that may be observable within image data. In implementations involving the use of OCT to acquire raw spectrum data, changes in optical path length may manifest themselves within the acquired raw spectra. Since these changes in optical path length are likely attributable to osmotic swelling, it is reasonable to view osmotic swelling and shrinking as processes that rearrange the distribution of scatterers within image elements in which swelling and/or shrinking occurs. Take for example a neuron that extends axially within a given image element. Neuronal swelling (shrinking) is likely to alter the transverse area spanned by this neuron, increasing (decreasing) it. Thus, by increasing (decreasing) the transverse area spanned by a neuron, neuronal swelling (shrinking) increases (decreases) the likelihood that photons traversing the image element in question will encounter scatterers, thereby leading to observed increases (or decreases) in optical path length. Under the aforementioned circumstances, while the distribution of scatterers may change significantly, the geometry of individual scatterers is unlikely to be altered in a significant way by activity-induced neuronal swelling. In this regard, some implementations of spectral variance methods allow for features indicative of neuronal activity to be obtained via method 1100.

Figure 12C:
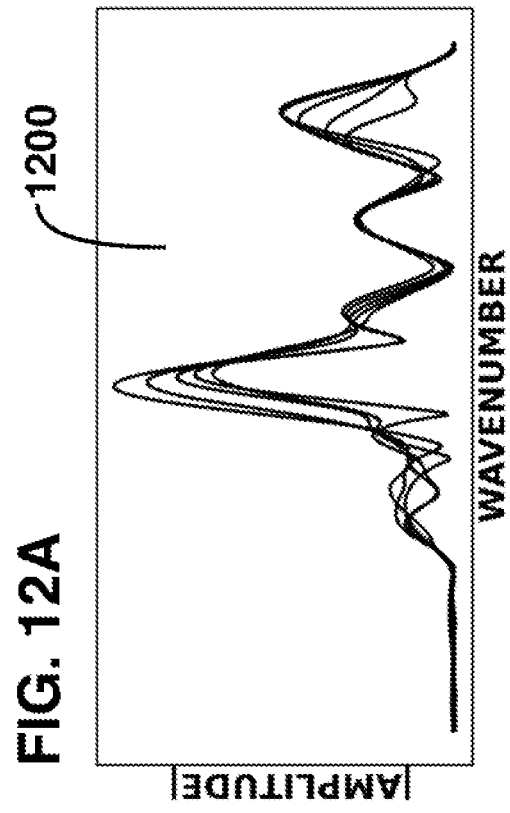
FIG. 12C illustrates a third spectrogram, according to some implementations of the present disclosure.
Figure 12D:
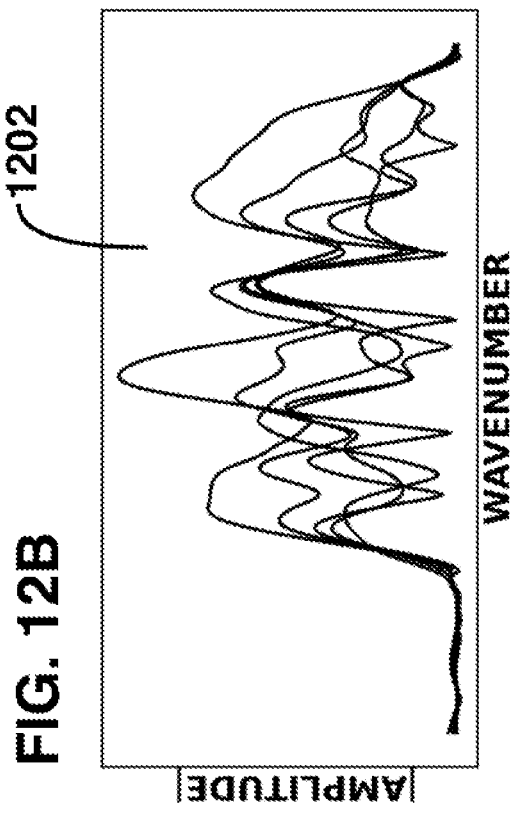
FIG. 12D illustrates a fourth spectrogram, according to some implementations of the present disclosure.

A filtered signal 906 displaying indications indicative osmotically-driven changes in cell volume is illustrated in FIG. 9D. A spectrogram 1204 associated with the filtered signal 906 is illustrated in FIG. 12C. The spectrogram 1204 displays normalized spectra indicating minimal shape variance within the spectrogram shown. Referring to FIG. 12D, an unnormalized spectrogram 1206 corresponding to the spectra associated with signal 906 is illustrated; observable therein is amplitude variance within the spectrogram. In the absence of pronounced shape variance, such scale variance can be interpreted as an indication indicative of changes in scatter density. Spectral variance methods may therefore be employed in a scale variance capacity to provide indications indicative of osmotically-driven changes in cell volume, which, in the neuronal layers of the retina, can serve as indications indicative of neuronal activity.

Figure 13:
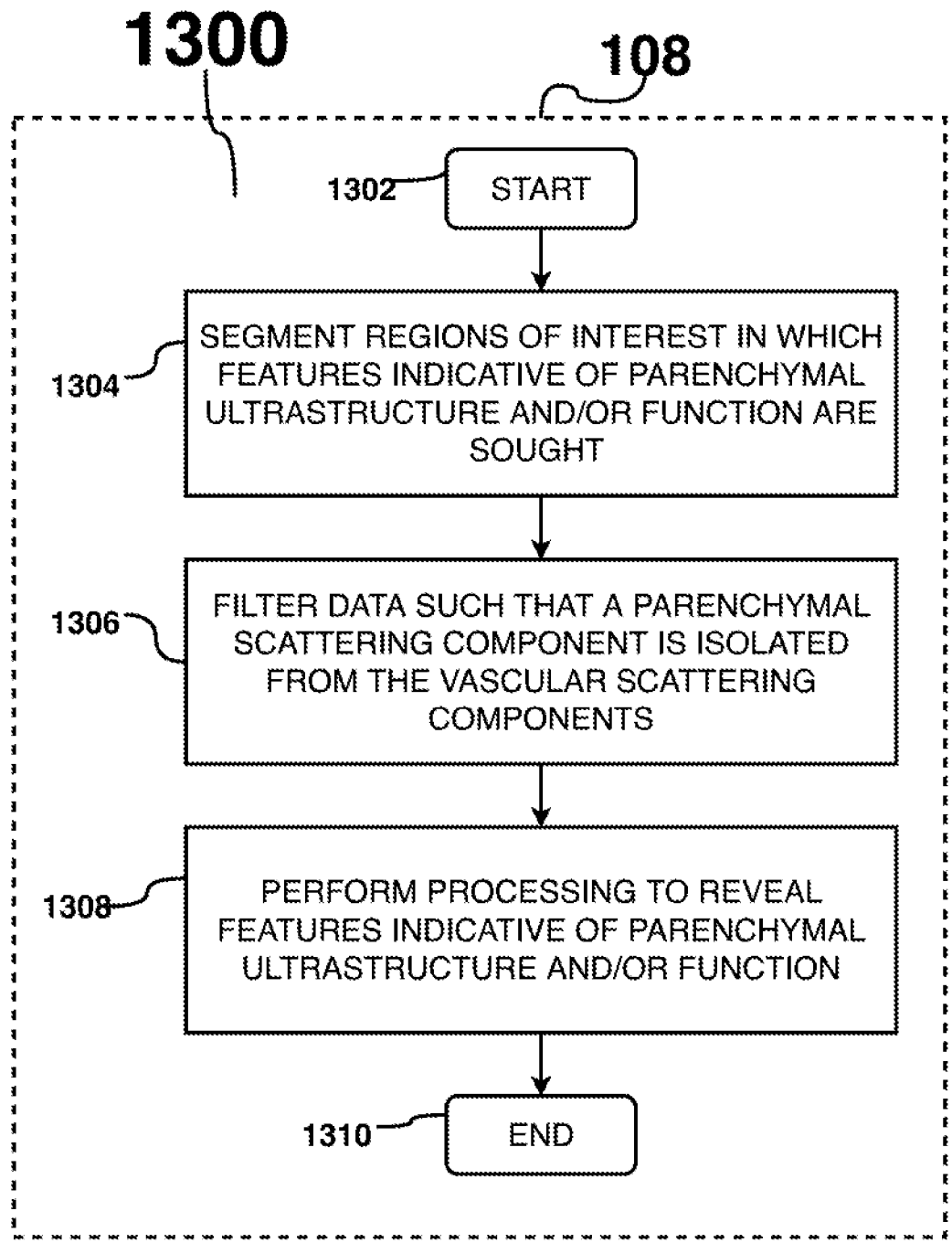
FIG. 13 is a process flow diagram for a method according to which features indicative of parenchymal ultrastructure and/or function can be obtained, according to some implementations of the present disclosure.

FIG. 13 illustrates a method 1300 for implementing step 108 of the method 100 (FIG. 1) capable of yielding features associated with parenchymal ultrastructure and/or function. Method 1300 begins with START 1302, according to which preprocessed image data outputted from step 106 is available to a processor. Subsequently step 1304 is performed. Step 1304 involves segmenting regions of interest (ROIs) in which features associated with parenchymal ultrastructure and/or function are sought. Implementations of step 1304 may thus include the segmentation of distinct retinal layers as ROIs. Additional implementations may involve the segmentation of ROIs within retinal layers of interest, such as the segmentation of axon bundles within the retinal nerve fiber layer. Non-retinal implementations may involve segmenting ROIs that correspond to axon bundles within the cornea.

Figure 14:
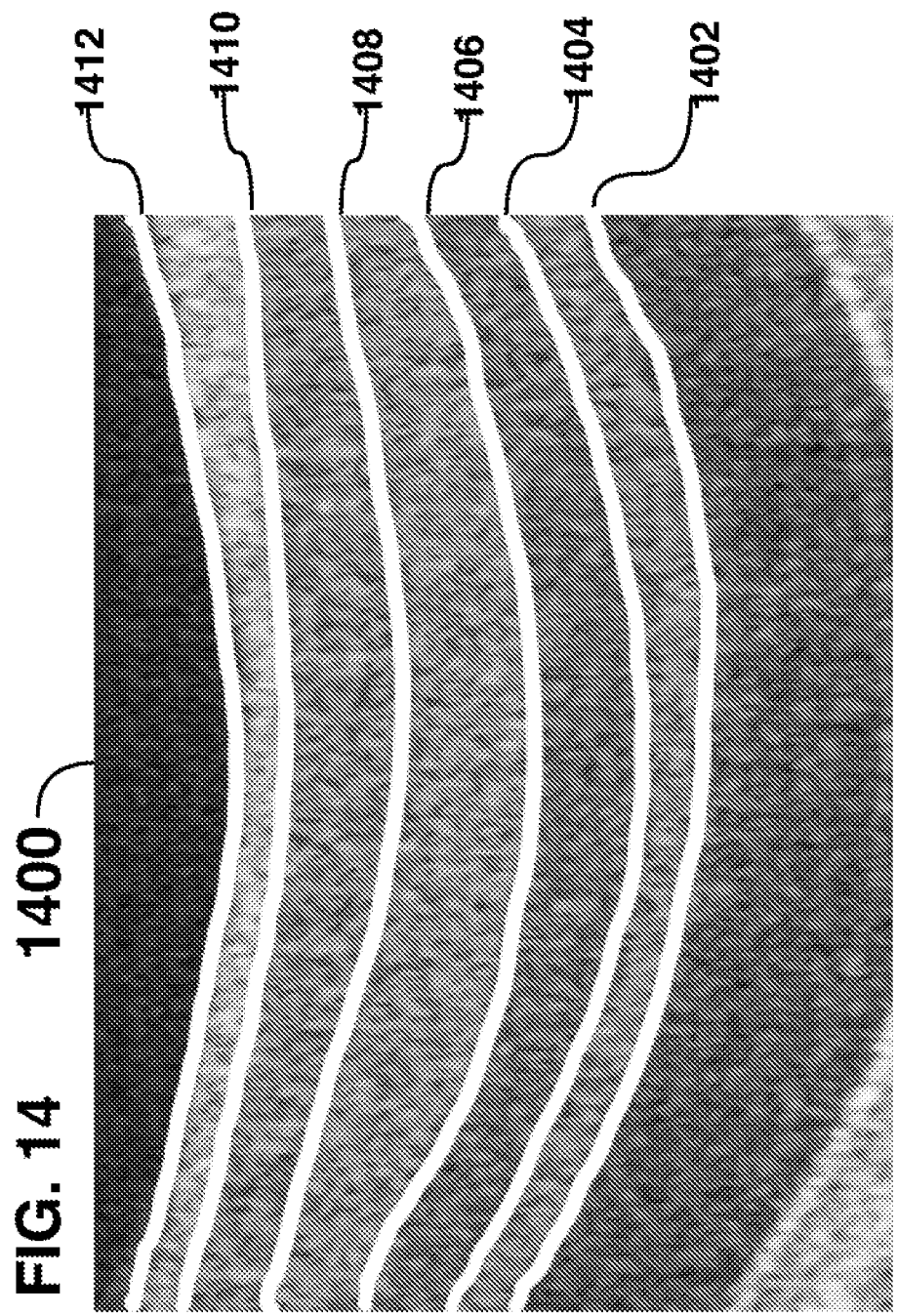
FIG. 14 illustrates an image of a retina segmented into its constituent layers, according to some implementations of the present disclosure.

Pertaining to retinal implementations of step 1304, layer-wise segmentation of a retinal sample is shown in FIG. 14, which includes a cross-sectional OCT B-scan 1400 of a human retina. Within the cross-sectional scan 1400, exemplary ROIs are segmented in a layer specific manner. Some implementations of the method 1300 are detailed with respect to the retinal nerve fiber layer and inner plexiform layer. The white line corresponding to 1406 denotes the outer boundary of the inner plexiform layer, and the white line corresponding to 1408 denotes the inner boundary of the inner plexiform layer. The inner plexiform layer thus corresponds to the cross-sectional region of the retina between 1406 and 1408. The white line corresponding to 1410 denotes the outer boundary of the retinal nerve fiber layer, and the white line corresponding to 1412 denotes the inner boundary of the retinal nerve fiber layer. The retinal nerve fiber layer thus corresponds to the cross-sectional region of the retina located between 1410 and 1412.

The subsequent step of method 1300, step 1306, involves filtering the preprocessed image data to isolate a parenchymal scattering component from the vascular scattering components. Step 1308 is next performed and involves processing image data to obtain features associated with parenchymal ultrastructure and/or function. Some implementations of step 1308 may not involve raw image data (e.g. some implementations involving method 2000), and may be restricted to the processing of preprocessed image data outputted from 106. Alternatively, processing step 1306 may be implemented such that the preprocessed image data, following segmentation and filtering via steps 1304 and 1306, is used to inform the processing of raw spectrum data; implementations along these lines provide an additional example of step 108 involving the processing of raw spectrum data by methods that are informed by the output of preprocessing step 106.

Figure 15:
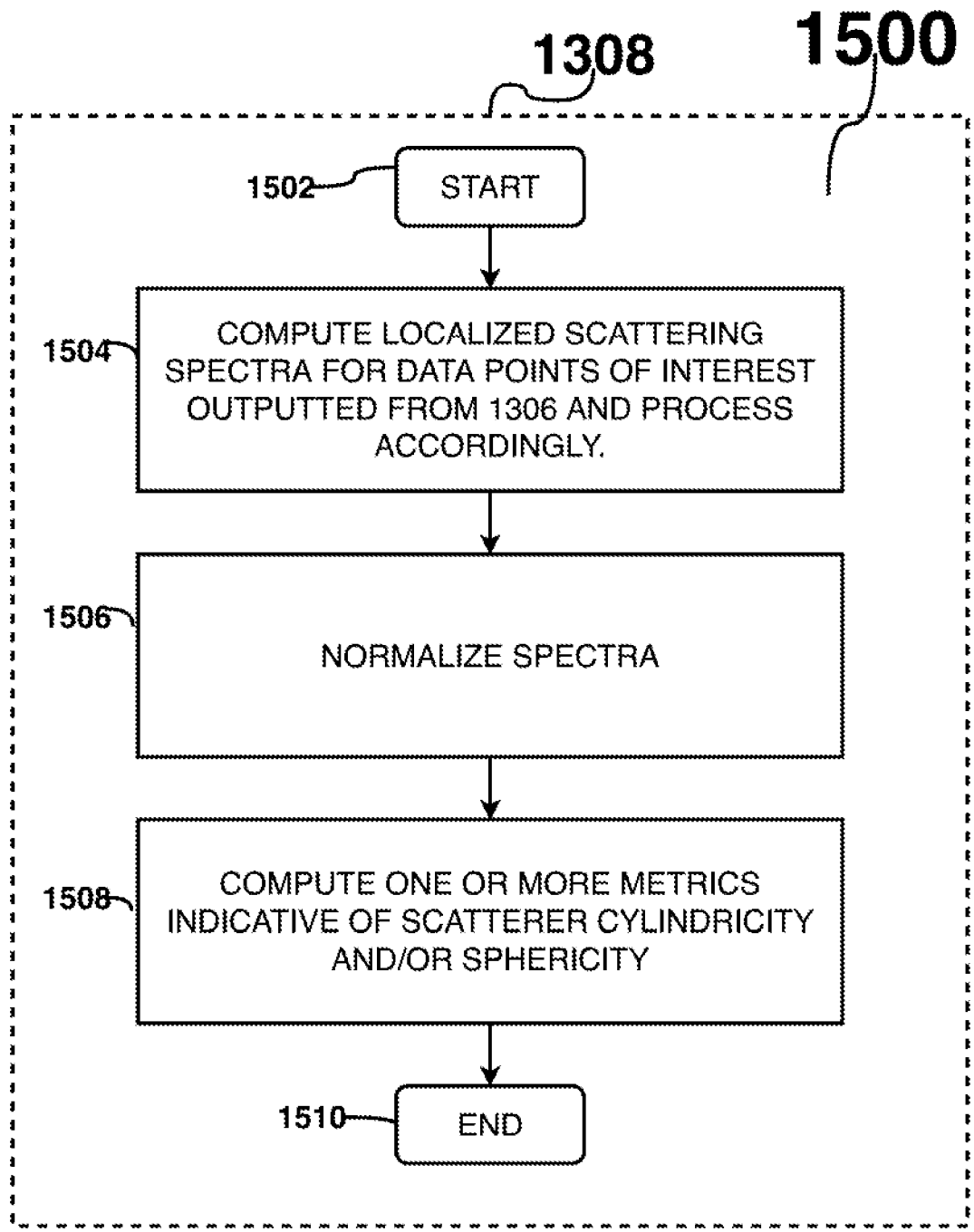
FIG. 15 is a process flow diagram for a method to spectroscopically determine one or more metrics indicative of scatterer cylindricity, sphericity, or both, according to some implementations of the present disclosure.

Referring to FIG. 15, a method 1500 for performing certain ultrastructural implementations of step 1308, in which the output of 1306 informs the processing of raw spectrum data, is illustrated. The method 1500 seeks to obtain spectroscopically derived features indicative of parenchymal ultrastructure. The method 1500 begins with START 1502 at which point raw spectrum data acquired during 104 may be made available to a processor. Subsequently, step 1504 specifies that the localized scattering spectra are computed for the data points of interest outputted from step 1306, and processed accordingly. In some implementations step 1504 can, at least in part, be accomplished via processing the raw spectrum data corresponding to the data points of interest via STFT. Step 1504 may also include the processing of localized scattering spectra. This processing of localized scattering spectra, may, for example, include the averaging, over space and/or time, of spectra obtained at a plurality of relevant data points. Averaging of localized scattering spectra corresponding to the same image element at a plurality of time points provides a means of minimizing the stochastic speckle fluctuations that are characteristically present in raw spectra obtained via OCT. Implementations of the method 1500 may also include normalization step as indicated by step 1506. Via normalization, features associated with parenchymal ultrastructure can be obtained in a relative manner, irrespective of variations in scatterer density (e.g. variations of mitochondrial density).

According to the localized scattering spectra obtained and processed by step 1504, and subsequently normalized via step 1506, features associated with parenchymal ultrastructure (e.g. mitochondrial ultrastructure) can be obtained. These features can be obtained by computing one or more metrics indicative of scatterer cylindricity and/or sphericity; such is indicated via step 1508. In some implementations, it may be advantageous to compute at least one metric indicative of scatterer cylindricity and at least one metric indicative of scatterer sphericity, such that sphericity versus cylindricity can be assessed. Metrics indicative of scatterer cylindricity and/or scatterer sphericity may be determined via decomposing the normalized scattering spectra inputted to step 1508. These scattering spectra, as they are associated with localized distributions of various subcellular scatterers (e.g. mitochondria, cell nuclei, axons, etc), can, by virtue of Mie scattering principles, be decomposed into a plurality of sub-spectrums that sum to the original scattering spectrums inputted to step 1508. For example, one sub-spectrum may be associated with a distribution of cylindrical scatterers and another associated with a distribution of spherical scatterers. Moreover, in accordance with step 1508 these sub-spectrums may be given weights that serve as metrics indicative of scatterer cylindricity and/or sphericity. It may be advantageous to obtain multiple metrics indicative of cylindricity, each cylindricity metric indicative of cylindrical geometries of different radii. Likewise, it may be of advantage to obtain multiple metrics indicative of sphericity, each sphericity metric indicative of spherical geometries of different radii. Implementations involving multiple metrics of cylindricity and/or sphericity can be used to obtain features associated with scatterer size as well as shape.

Some implementations may employ artificial intelligent and/or machine learning algorithms or techniques to decompose scattering spectra into a plurality of weighted sub-spectrums, the weights of which may be indicative of scatterer cylindricity and/or sphericity. Method 1500 concludes with END 1510, and metrics indicative of scatterer cylindricity and/or sphericity may be outputted. When the method 1500 is employed to accomplish method 1300, step 1510 thus concludes 1300, as the obtained metrics indicative of scatterer cylindricity and/or sphericity may be taken as features indicative of parenchymal ultrastructure.

According to some implementations, it may be of utility to employ method 1500 to obtain features indicative of parenchymal ultrastructure within the retinal nerve fiber layer. In these implementations, the method 1500 may be provided (via steps 1304 and 1306) with preprocessed data segmented to be localized within the retinal nerve fiber layer and filtered to remove vascular scattering components. Within the retinal nerve fiber layer axons fasciculate to form arcuate bundles of regularly spaced axons. Furthermore, when imaged through the eye's pupil, as is common practice with OCT, these axons and axon bundles tend to assume a transverse orientation with respect to the imaging beam. Stemming from these anatomical characteristics it is reasonable to predict that the localized scattering spectra obtained from image elements within the retinal nerve fiber layer will be significantly more cylindrical than spherical. In instances of disease, however, axons are known to degenerate, axonal varicosities are known to swell, and axonal mitochondria are known to fragment. These above pathological manifestations can alter the relative proportion of cylindrical and spherical scatterers within the retinal nerve fiber layer. Thus, metrics of scatterer cylindricity and sphericity outputted by step 1508, which serve as features indicative of parenchymal ultrastructure per the method 1300, can be interpreted as features of disease in accordance with step 108. In this regard, relevant features associated with disease may include but are not limited to mitochondrial fragmentation, axonal swelling, axonal degeneration, or any combination thereof. Moreover, by obtaining multiple metrics associated with sphericity, it may be possible to differentiate axonal swelling from mitochondrial fragmentation, as mitochondrial fragmentation tends to be associated with smaller spherical scatterers than axonal swelling.

More generally, the method 1500 can be implemented to accomplish image segmentation tasks, particularly those involving segmentation of OCT data. In this regard, metrics of scatterer cylindricity and sphericity are expected to vary within and/or between retinal layers. Accordingly, 1500 may be employed to segment individual axon bundles within the retinal nerve fiber layer. Likewise, method 1500 may be employed to segment axon bundles within the cornea. Furthermore, cylindricity versus sphericity metrics obtained via 1500 may be used to segment the retinal ganglion cell layer from the inner plexiform layer; these layers lie adjacent to each other and are difficult to segment using existing methods. Depicted in 1400 is a ganglion cell layer, which houses the somas of retinal ganglion cells, and lies between lines 1410 and 1408. Beneath the ganglion cell layer lies the inner plexiform layer, which stratifies between 1408 and 1406. Looking at only image intensity values (e.g. those found in typical A-scans) these layers are difficult to discriminate from one another. However, by using spectroscopic insights, especially those insights provided by one or more metrics indicative of cylindricity and/or sphericity, differences between these layers may become accentuated, thus allowing for better discrimination. Specifically, since the inner plexiform layer tends to contain primarily axonal and dendritic processes, it is expected to display increased cylindricity relative to sphericity when compared to the ganglion cell layer, which tends to contain a high density of spherically-shaped cell bodies and nuclei. To this end, foreseeable implementations of 1300 may employ method 1500 twice: once during step 1304 and once during step 1308.

Metrics indicative of cylindricity and/or sphericity can be used to generate a distribution mapped upon an n-dimensional space (i.e. a space consisting of one or more dimensions), the integer n corresponding to the number of metrics used to define the mapping space. One such implementation is described in which one metric of sphericity and one metric of cylindricity serve as the basis according to which a distribution of points is mapped upon a two dimensional space. Distributions of this nature may be interpreted to assess cylindricity versus sphericity within a distribution of image elements, such as image elements within the retinal nerve fiber layer. In these instances, it may be advantageous to characterize a distribution according to one or more mathematical functions. To this end, the centroid of a distribution may provide features indicative of the ultrastructure of the retinal nerve fiber layer. In particular, the centroid of a distribution yields parameters corresponding to the averages of the metrics used to define the mapping space. For example, a healthy retinal nerve fiber layer is expected to be associated with a distribution centroid tending towards cylindricity whereas a distribution centroid that is shifted towards sphericity may be associated with disease, potentially indicative of mitochondrial fragmentation, axonal swelling, and/or axonal degeneration.

Figure 16A:
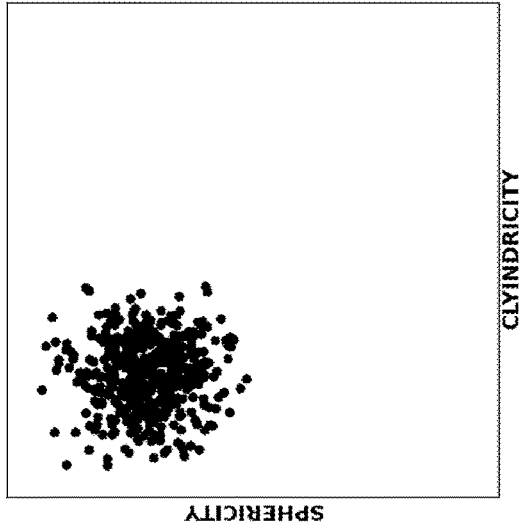
FIG. 16A illustrates point-wise distribution comparing cylindricity versus sphericity wherein the distribution tends towards cylindricity, according to some implementations of the present disclosure.
Figure 16B:
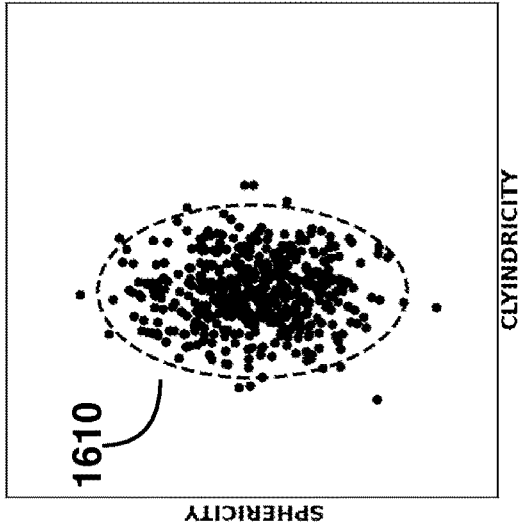
FIG. 16B illustrates point-wise distribution comparing cylindricity versus sphericity wherein the distribution tends towards sphericity, according to some implementations of the present disclosure.

FIG. 16A illustrates a first distribution 1600 and FIG. 16B illustrates a second distribution 1602. In both the first distribution 1600 and the second distribution 1602, the mapping space consists of one metric indicative of scatterer cylindricity and one metric indicative of scatterer sphericity. The centroid of the first distribution 1600 tends towards cylindricity, and thus provides indications indicative of a sample likely to contain a greater proportion of cylindrical scatterers relative to spherical scatterers; a healthy retinal nerve fiber layer is expected to be associated with such a distribution. Alternatively, the centroid of the second distribution 1602 tends towards sphericity, and thus provides indications indicative of a sample likely to contain a greater proportion of spherical scatterers relative to cylindrical scatterers. In cases in which the second distribution 1602 is drawn from image elements within a retinal nerve fiber layer, the second distribution 1602 may be interpreted to contain features indicative of axonal pathology, such as axonal swelling and mitochondrial fragmentation.

The method 1300 can likewise be employed to obtain features indicative of parenchymal ultrastructure from within the inner and/or outer plexiform layers of the retina. In these implementations, step 1304 involves segmenting the inner and/or outer plexiform layer (e.g. as described above using method 1500). Step 1306 remains the same. Pertaining to step 1308, the analyses described herein can take into account the anatomical organization of the synaptic layers of the retina (i.e. the inner and outer plexiform layers). Implementations are detailed with respect to the inner plexiform layer, however, other implementations may extend to the outer plexiform layer in a straightforward manner.

The inner plexiform layer tends to adopt a spatially regular anatomical organization; scatterers (e.g. mitochondria) are thus expected to be uniformly distributed across proximal image elements (e.g. those contained in single B-scan). This expectation may fail to hold in pathological instances in which synaptic dropout, dendritic atrophy, and/or neuro-inflammation may be present. Accordingly, implementations of step 1308 pertaining to the obtainment of features indicative of parenchymal ultrastructure within the inner plexiform layer may be structured as methods to assess how uniformly distributed scatterers are within the inner plexiform layer.

Distinct advantage may be acquired by modifying method 1500 to include implementations of step 1308 pertaining to the inner plexiform layer. In these implementations, features indicative of the distribution of scatterers across the one or more inner plexiform layer cross-sections (e.g. segmented B-scans) can be obtained. To accomplish this, one or more metrics indicative of scatterer sphericity and/or cylindricity may be computed for a plurality of image elements localized within the inner plexiform layer, and likewise used to generate a distribution of points in an n-dimensional space. Again, an implementation is described according to a two-dimensional space with a first dimension corresponding to scatterer cylindricity and a second dimension corresponding to scatterer sphericity. Such a two-dimensional distribution of points may be characterized as a multivariate Gaussian distribution and/or elliptical function. Characterization via a multivariate Gaussian distribution yields one or more parameters indicative of the average of one or more metrics, or a combination of metrics. For example, via characterization according to a two-dimensional Gaussian function, a first parameter may be indicative of the average of the first metric (e.g. cylindricity) and a second parameter may be indicative of the average of the second metric (e.g. sphericity). Moreover, Gaussian characterization can yield one or more parameters indicative of the variance of one or more metrics, or a combination of metrics. In the case of characterization via a two-dimensional Gaussian function, a first parameter may be indicative of the variance of the first metric (e.g. cylindricity), second parameter may be indicative of the variance of the second metric (e.g. sphericity), and a third parameter (e.g. a covariance derived parameter) may be indicative of the variance of both the first and second metrics. Via elliptical characterization, parameters associated with the average and/or variance of one or more metrics, or combination of metrics, may likewise be provided. For example, an elliptical fit typically yields both a first radius parameter and a second radius parameter, both of which can be associated with the variance of one or more metrics. Moreover, by comparing the first and second radius parameters, it is possible to provide indications of an ellipse's deviation from circularity; deviation from circularity can provide an indication of covariance between the first and second metric.

Figure 16C:
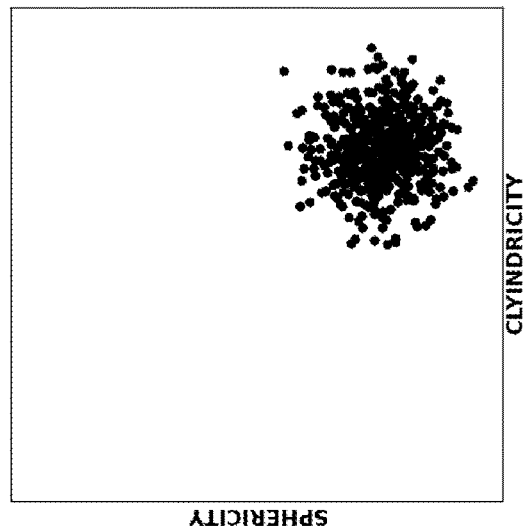
FIG. 16C illustrates point-wise distribution comparing cylindricity versus sphericity wherein the distribution tends toward uniformity, according to some implementations of the present disclosure.
Figure 16D:
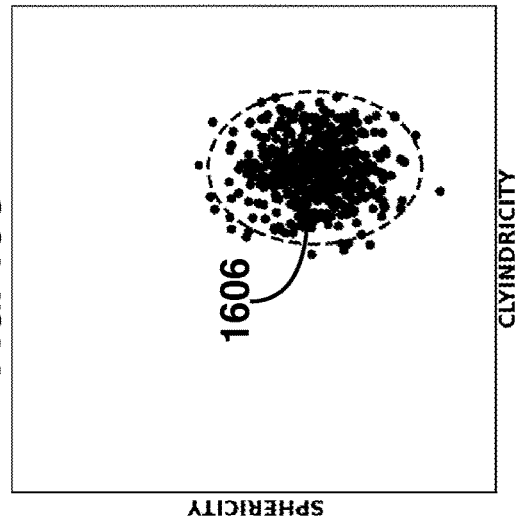
FIG. 16D illustrates a point-wise distribution comparing cylindricity versus sphericity wherein the distribution tends toward disuniformity, according to some implementations of the present disclosure.

In accordance with the method 1300, the parameters yielded by characterizing a distribution as described above can aid in identifying features indicative of parenchymal ultrastructure. FIG. 16C illustrates a third distribution 1604 and FIG. 16D illustrates a fourth distribution 1606. The third distribution 1604 (FIG. 16C) corresponds to a distribution of image elements drawn from a first segmented inner plexiform layer, each element therein associated with a first metric indicative of cylindricity and a second metric indicative of sphericity, and mapped to the two-dimensional space shown. The fourth distribution 1608 (FIG. 16D) corresponds to a distribution of image elements drawn from a second segmented inner plexiform, each element therein associated with a first metric indicative of cylindricity and a second metric indicative of sphericity, and mapped to the two-dimensional space show. The third distribution 1604 and the fourth distribution 1608 are shown characterized according to elliptical fits 1606 and 1610, respectively. The fit 1606 indicates that the third distribution 1604 that tends towards circularity whereas the fit 1610 indicates that the fourth distribution 1608 deviates away from circularity. Interpretation of the fourth distribution 1608 based at least in part on the fit 1610 can provide features of associated disease. In particular, the fit 1610 displays a significantly larger radius value along the sphericity axis than the cylindricity axis. Such can be taken as a feature of scatter disuniformity (and/or hyper-sphericity) and may be interpreted to provide indications indicative of biomarkers including synaptic dropout, dendritic atrophy, neuro-inflammation, or any combination thereof.

Another foreseeable implementation for accomplishing step 1308 to obtain features indicative of parenchymal ultrastructure is to generate a distribution of image data values in the form of an n-dimensional histogram. Image data values may include but are not limited to the following: intensity values from a single B-scan, intensity values temporally averaged over a stack of spatially overlapping B-scans, and spectroscopically derived (e.g. via method 1500) metrics indicative of cylindricity and/or sphericity.

Figure 17A:
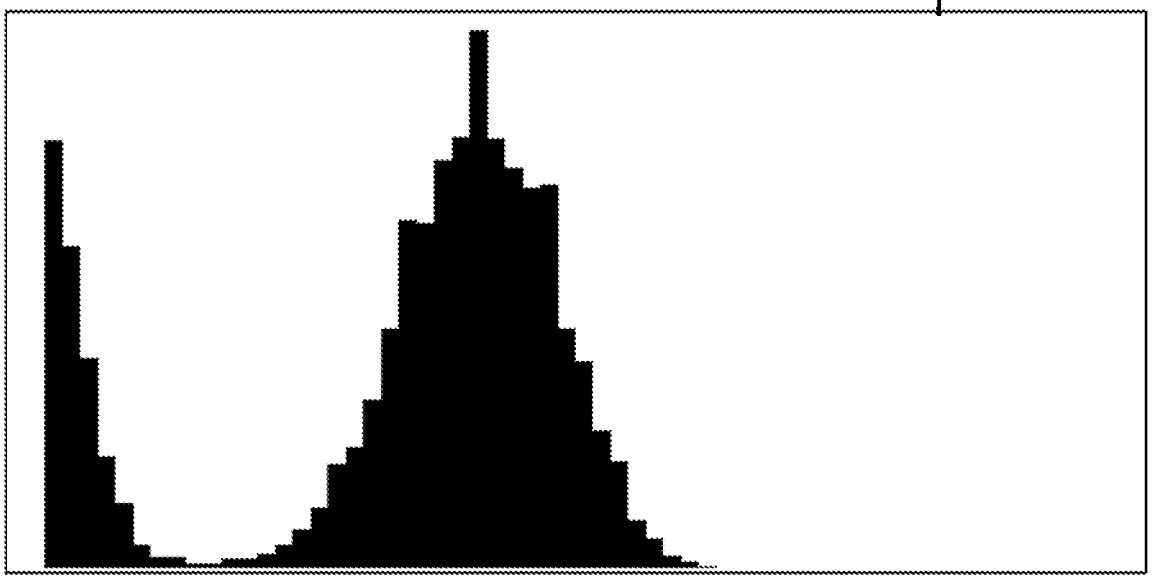
FIG. 17A illustrates a histogram of image values corresponding to a normative image data set, according to some implementations of the present disclosure.
Figure 17B:
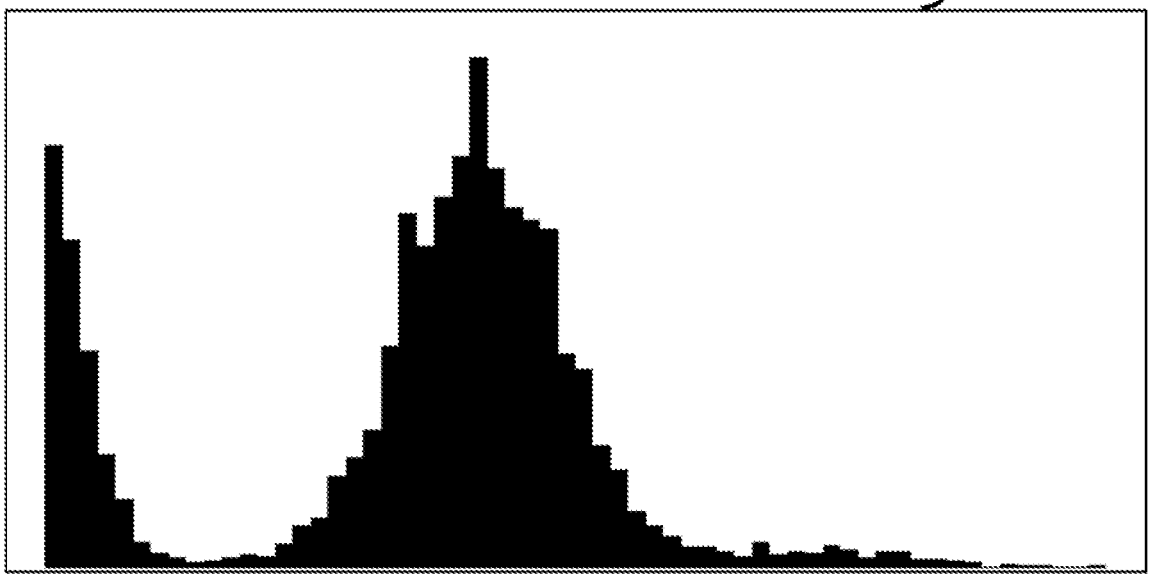
FIG. 17B shows a histogram of image data corresponding to an individual subject, according to some implementations of the present disclosure.

When generating histograms from image values, values corresponding to zero and/or values below an arbitrary threshold may be excluded from a generated histogram. Implementations involving the mapping of data to a one-dimensional histogram are herein detailed. A first one-dimensional histogram 1700 is illustrated in FIG. 17A, 1700 and a second one-dimensional histogram 1702 is illustrated in FIG. 17B. Both histograms 1700 and 1702 are drawn from elements within the inner plexiform layer of the retina, and generated using a metric indicative of scatterer sphericity. The first histogram 1700 can be taken as drawn from a normative dataset to indicate a distribution of scatterer sphericity expected in a healthy retinal inner plexiform lacking apparent pathology. The second histogram 1702 can be taken as drawn from a subject displaying features indicative of pathology within the inner plexiform layer of their retina. The first and second histograms 1700 and 1702 are both displayed on identically scaled axes, and the bins of each are equal in width. The height of each bar is proportional to the number of elements in each bin, and the horizontal axis scales with a sphericity metric.

The shape of a generated histogram may be characterized via a mathematical model specifying one or more arbitrary mathematical functions. For example, a histogram distribution may be treated as a single distribution or as the sum of a plurality of separate distributions. Accordingly, the first and second histograms 1700 and 1702 may be characterized as sums of three separate distributions.

Implementations employing histogram distribution analysis with respect to scatterer sphericity are described. The first and second histograms 1700 and 1702 thus represent distributions of scatterer sphericity and are characterized as sums three separate distributions: one distribution corresponding to image elements displaying a below average contribution from spherical scatterers, a second distribution corresponding to elements displaying average and/or median contribution from spherical scatterers, and a third distribution corresponding to elements displaying above average contribution from spherical scatterers.

Figure 18:
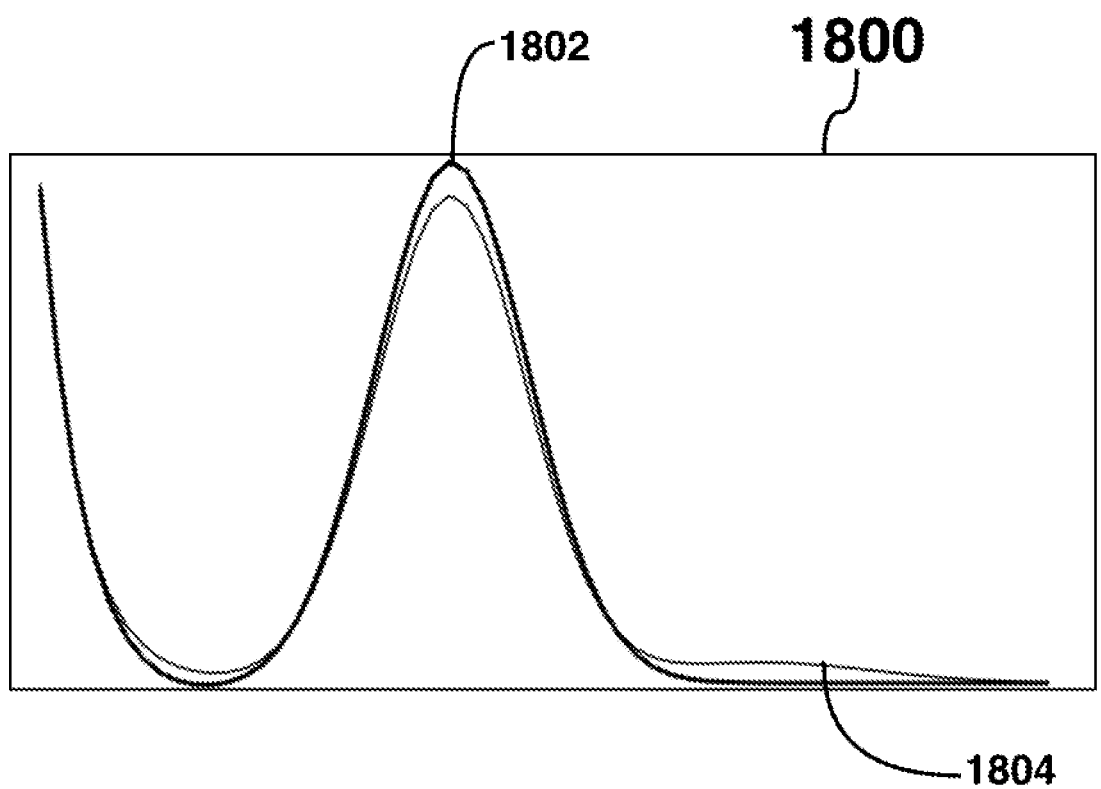
FIG. 18 contains a plot including a first curve characterizing the histogram of FIG. 17A and a second curve characterizing the histogram in FIG. 17B, according to some implementations of the present disclosure.

The first and second histograms 1700 and 1702 have been characterized according to the three-distribution model described above. Referring to FIG. 18, the results of this characterization are shown in plot 1800. The plot 1800 includes a first trace 1802, the thicker of the two traces, which shows the fitted representation of the histogram 1700, and a second trace 1804, the thinner of the two traces, which shows the fitted representation histogram 1702. The axes of the plot 1800 have the same scale as the first and second histograms 1700 and 1702 (FIGS. 17A and 17B).

Noting that each of the first trace 1802 and the second trace 1804 in the plot 1800 are, as specified herein, sums of three separate distributions, the relative contributions from each of the separate distributions (with respect to the cumulative distribution) may be interpreted as features indicative of parenchymal ultrastructure. To this end, the three separate distributions that sum to produce the first trace 1802 and the second trace 1804 are shown individually via FIGS. 19A-19C. The axes in FIGS. 19A-19C are scaled identically to the axes in the plot 1800.

Figure 19A:
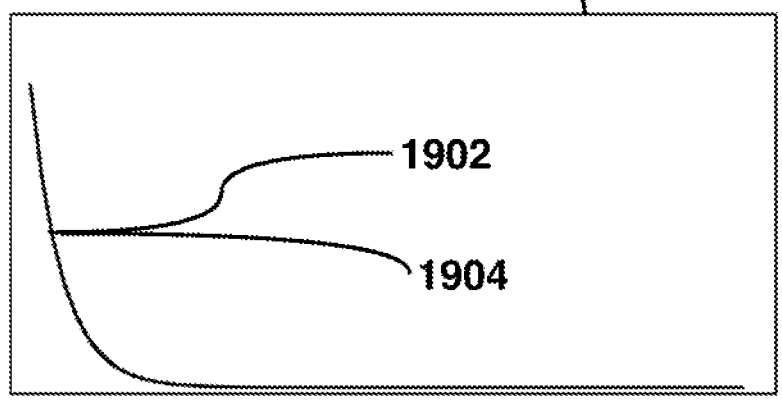
FIG. 19A illustrates a pair of fitted curves characterizing the distributions of elements displaying below average values in FIGS. 17A and 17B, according to some implementations of the present disclosure.

FIG. 19A, 1900, shows fits corresponding to the distributions of elements displaying below average scatterer sphericity. The single bold curve therein is actually two curves that, within the scale of the figure, are indistinguishable from one another. Thus, the bold curve in 1900 corresponds to two figure elements: 1902 and 1904. The curve denoted by 1902 represents a fit to the distribution of elements displaying below average scatterer sphericity in histogram 1700, and 1904 represents a fit to the distribution of elements displaying below average scatterer sphericity in histogram 1702.

Figure 19B:
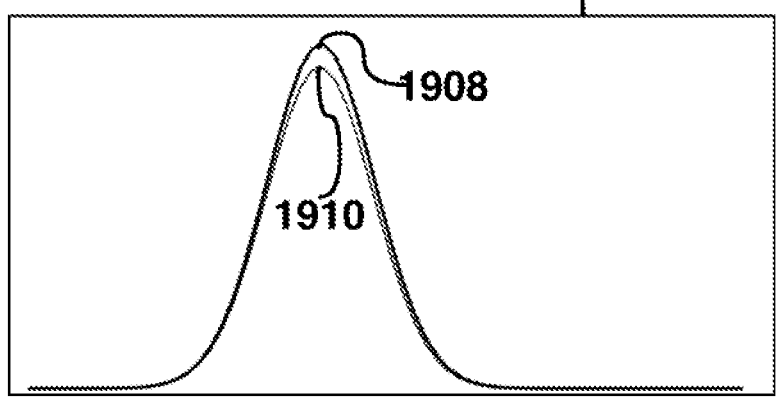
FIG. 19B illustrates a pair of fitted curves characterizing the distributions of elements displaying average and median values in FIGS. 17A and 17B, according to some implementations of the present disclosure.

Referring to FIG. 19B, a plot 1906 shows fits corresponding to the distributions of elements displaying average and/or median scatterer sphericity. Evident in the plot 1906 is that the two curves are distinguishable. A first curve 1908 fits the distribution of elements within the first histogram 1700 (FIG. 17A) displaying average and/or median scatterer sphericity, and a second curve 1910 fits elements within the second histogram 1702 (FIG. 17B) that display average and/or median scatterer sphericity.

Figure 19C:
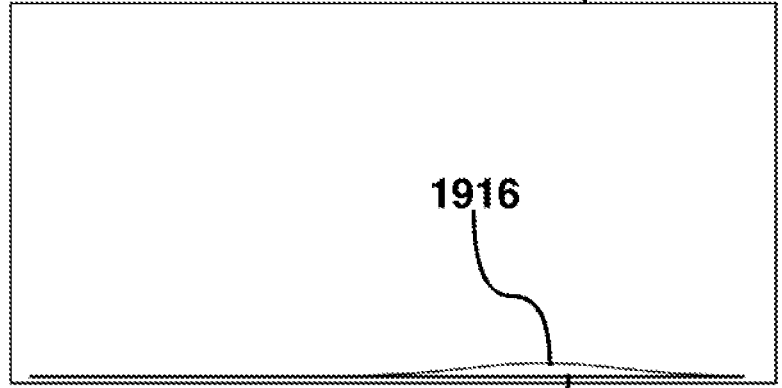
FIG. 19C illustrates a pair of fitted curves characterizing the distributions of elements displaying above average values in FIGS. 17A and 17B, according to some implementations of the present disclosure.

Referring to FIG. 19C, a plot 1912 shows fits corresponding to the distributions of elements displaying above average scatterer sphericity. A first curve 1914 fits the distribution of elements within the first histogram 1700 (FIG. 17A) displaying above average scatterer sphericity, and a second curve 1916 fits the distribution of elements displaying above average scatterer sphericity within the second histogram 1702 (FIG. 17B).

According to some implementations, numerical integration may be used to quantitatively determine the relative contributions of each separate distribution (e.g., those plotted in FIGS. 19A-19C) with respect to the cumulative distributions shown in FIG. 18. Unto this notion, all of the curves in FIG. 18 and FIGS. 19A-19C have been numerically integrated to quantify these relative contributions. That is, the relative contributions of 1902, 1908 and 1914 to 1802, and the relative contributions of 1904, 1910, and 1916 to 1804, have been computed via numerical integration. Normalized results of the aforementioned numerical integration are provided in TABLE 1.

TABLE 1

| Data Source | 1700 | 1702 |
|---|---|---|
| Contribution from below average scatterer sphericity | 0.172 | 0.179 |
| Contribution from average scatterer density sphericity | 0.828 | 0.775 |
| Contribution from above average scatterer sphericity | 0.000 | 0.046 |

TABLE 1 quantitatively summarizes the results of the histogram distribution analysis described above. Numerical results in TABLE 1 show, for the data in the first and second histograms 1700 and 1702 (FIGS. 17A-17B), the percent contributions of each of the three separate distributions with respect to the cumulative distributions they sum to. That is, the three separate distributions that sum to form 1802 and 1804 must account for all (100 percent) of the elements used to generate the first and second histograms 1700 and 1702, respectively. Increased contribution from above average scatterer sphericity in the second histogram 1702 compared with the first histogram 1700 may provide indications indicative of biomarkers including synaptic dropout, dendritic atrophy, neuro-inflammation, or any combination thereof.

Parameters obtained by characterizing a histogram distribution may likewise be interpreted as features indicative of parenchymal ultrastructure. In a foreseeable implementation, the distribution corresponding to below scatterer sphericity is fitted as an exponential decay in the form: $f(x)=a_1*\exp(-b_1*x)$, [Equation 1]; the distribution corresponding to average and/or median scatterer sphericity is modeled in the form: $g(x)=a_2*\exp((-1*(x-b_2)/c_2)^2$, [Equation 2]; and the distribution corresponding to above average scatterer sphericity is modeled as: $h(x)=a_3*\exp((-1*(x-b_3)/c_3)^2$, [Equation 3]. In all equations the variable x corresponds to image data value (which, in the implementations described herein, is a sphericity metric), whereas the subscripted parameters (e.g. $a_1$) combine to determine the shape and position of the fit.

In some implementations histogram distribution characterization may be extended to yield multi-color images. To this end, the relative contribution from each of the three distributions described above may be associated with a color, such as red (R), green (G), or blue (B). As such, data outputted via histogram distribution characterization may foreseeably be displayed as an RGB image, thus providing spatial context to the output. Furthermore, metrics indicative of scatterer cylindricity and/or sphericity can likewise be employed to generate RGB image data, and may thus allow a generic output from method 1500 to be placed into a spatial context.

Figure 20:
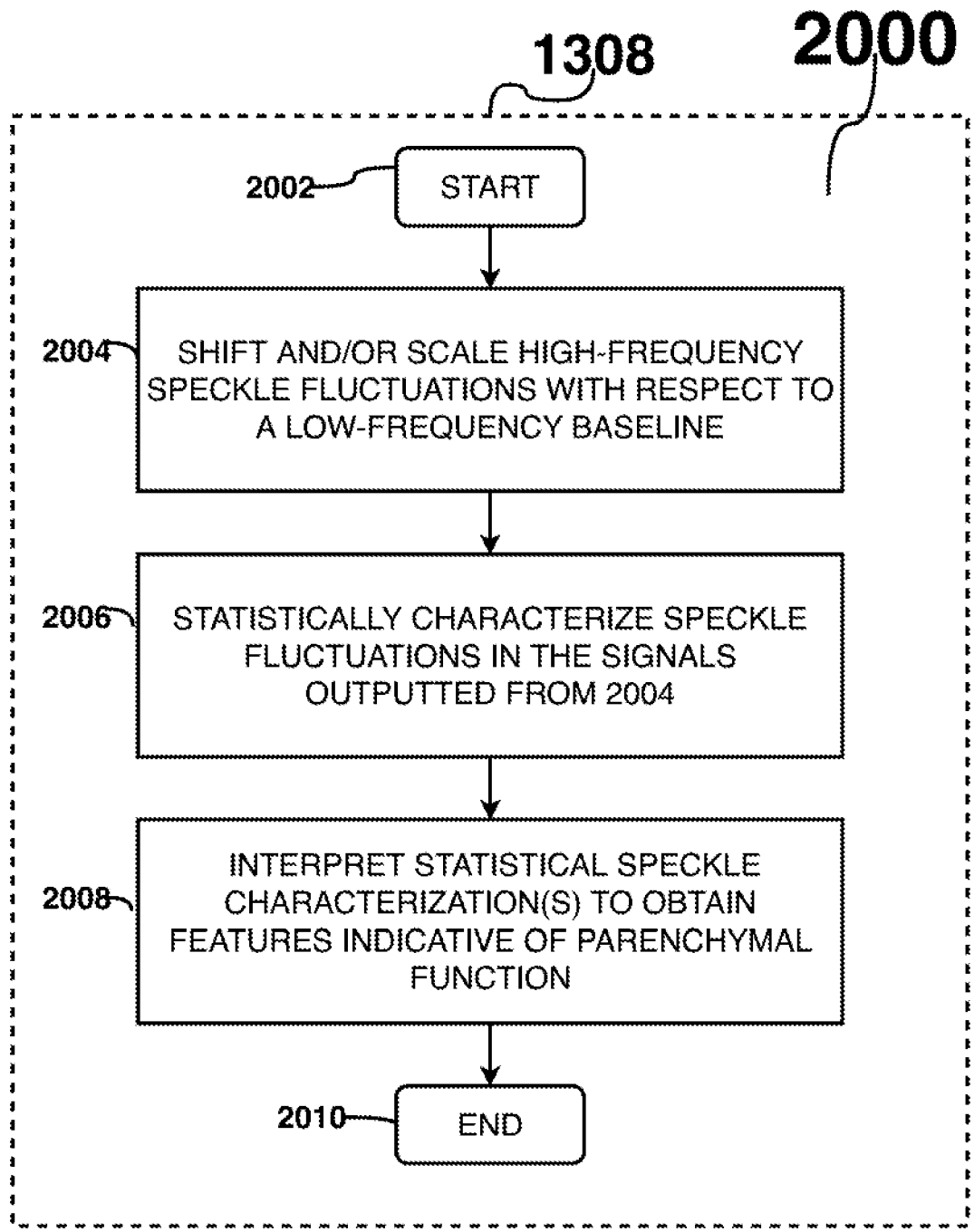
FIG. 20 is a process flow diagram for a method to assess parenchymal function via statistically characterizing speckle fluctuations, according to some implementations of the present disclosure.

Implementations of method 1300 may involve obtaining features indicative of parenchymal function (e.g. intracellular transport). Regarding these implementations, step 1308 is summarized accordingly in FIG. 20, 2000. Method 2000 leverages the notion that time-varying parenchymal processes can influence stochastic speckle fluctuations within the acquired image data. These fluctuations, being stochastic, can be statically characterized when image data is acquired at a sufficient number of time points. Accordingly, by statistically characterizing speckle fluctuations within tissue parenchyma, features associated with parenchymal function can be obtained; this is the essence of method 2000.

Method 2000 begins with step 2002, START, at which point the isolated parenchymal component outputted from step 1306 is available to a processor. Subsequently, step 2004 is performed and high frequency speckle fluctuations may be shifted and/or scaled with respect to a low frequency baseline. Shifting allows speckle fluctuations to be characterized irrespective of slow signal drift. Scaling allows the amplitude of speckle fluctuations to be characterized relative to the average signal value about which speckle fluctuations occur. High average signal values may indicate a high density of scatterers, which may increase the amplitude of the associated speckle fluctuations. The opposite may be true for average signal values that are low. Scaling may therefore allow speckle fluctuations to be characterized in a relative manner. Next, step 2006 is performed and speckle fluctuations are statistically characterized. After speckle fluctuations have been statistically characterized via step 2006, step 2008 is performed, and a statistical characterization of speckle fluctuation may be interpreted to obtain features indicative of parenchymal function. Once features indicative of parenchymal function have been obtained step 2010 END is reached; these features may then be outputted for subsequent interpretation.

Figure 21A:
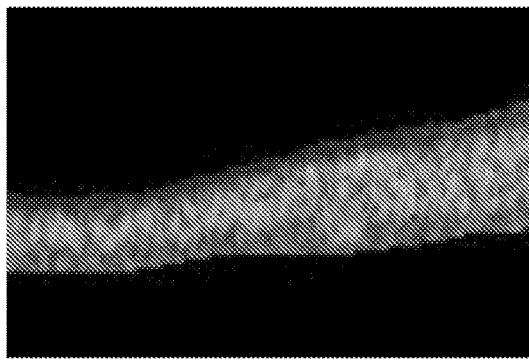
FIG. 21A shows a segmented cross-section of a retinal nerve fiber layer, according to some implementations of the present disclosure.
Figure 21B:
FIG. 21B illustrates an identification of axon bundles within the retain nerve fiber layer of FIG. 21A, according to some implementations of the present disclosure.
Figure 21C:
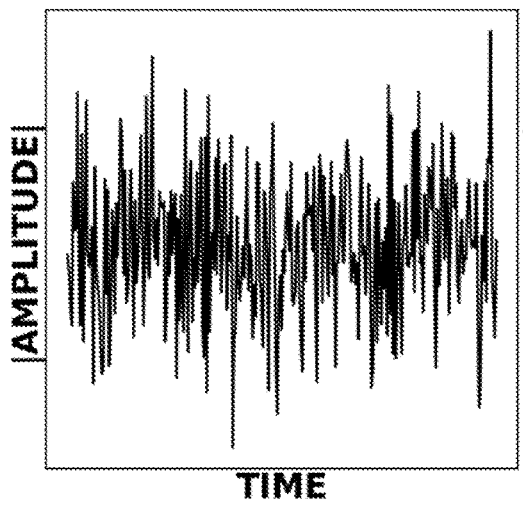
FIG. 21C illustrates a signal displaying speckle fluctuations indicative of normal axonal transport, according to some implementations of the present disclosure.
Figure 21D:
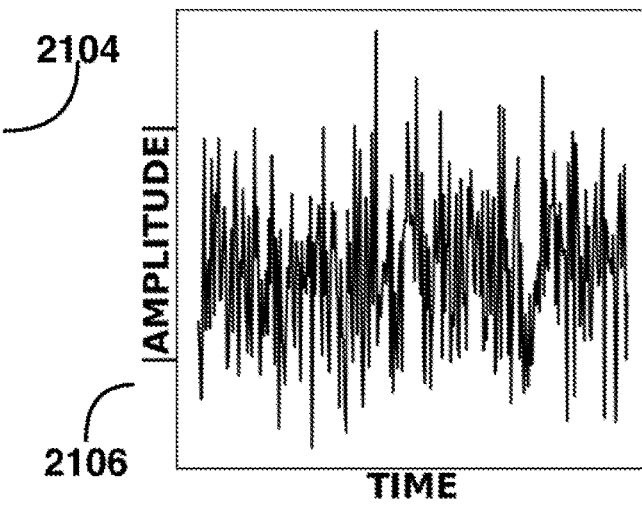
FIG. 21D illustrates a signal displaying speckle fluctuations indicative of altered axonal transport, according to some implementations of the present disclosure.
Figure 21E:
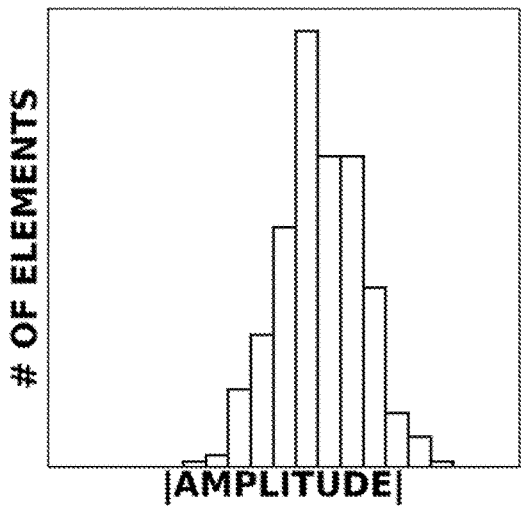
FIG. 21E illustrates a histogram of speckle amplitudes contained in FIG. 21C, according to some implementations of the present disclosure.
Figure 21F:
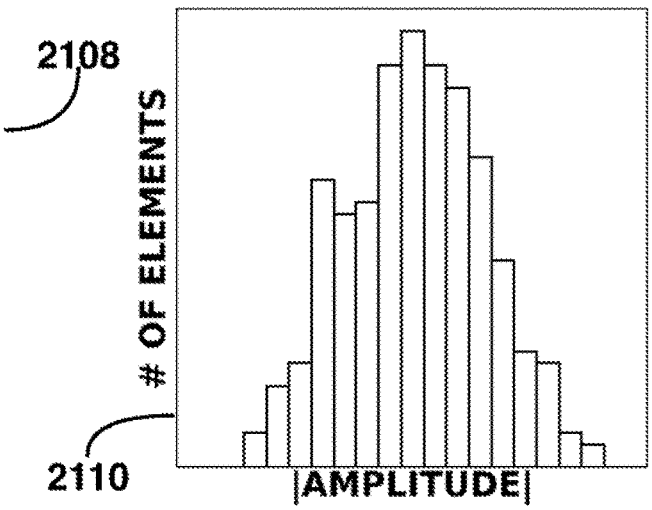
FIG. 21F illustrates a histogram of speckle amplitudes contained in FIG. 21D, according to some implementations of the present disclosure.

Some implementations may employ method 2000 to obtain features indicative of axonal transport. According to these implementations, ROIs segmented per step 1304 should contain axons. Axon-containing ROIs may include the cornea or retinal nerve fiber layer. To this end, FIG. 21A illustrates an OCT B-scan 2100 segmented to contain only the retinal nerve fiber layer. Furthermore, it may be advantageous to segment ROIs corresponding to axon bundles within the retinal nerve fiber layer; such can be accomplished via employing method 1500 in a segmentation capacity. Accordingly, axon bundles within the OCT B-scan 2100 have been segmented 2102 in FIG. 21B.

Signals corresponding to image elements within axon-containing ROIs can be shifted and scaled per step 2004. Exemplary shifted and scaled signals outputted from 2004 are shown via FIG. 21C, 2104, and FIG. 21D, 2106. The signals indicated in 2104 and 2106 provide speckle fluctuations that can be statistically characterized according to step 2006. In some implementations step 2006 may involve characterizing speckle fluctuations via histograms. Histograms characterizing speckle amplitude distributions are shown in FIG. 21E, 2108, and FIG. 21F, 2010. Histogram 2108 was generated using data shown in signal 2104 and histogram 2110 was generated using the data shown in signal 2106. Histograms 2108 and 2110 can be interpreted to obtain features indicative of axonal transport. Histogram 2108 shows a distribution of speckle fluctuation amplitudes indicative of normal axonal transport. Relative to 2108, histogram 2110 has a larger variance and reduced mean; such may be an indication indicative of altered axonal transport.

Step 108 concludes once features associated disease have been obtained. According to some implementations, 108 involves obtaining a plurality of features associated with disease. Subsequently, step 110 is performed and features associated with disease are outputted. At this point the features obtained step 108 may be combined with non-image-based features obtained during acquisition step 104. For example, eye movements in response to saccade-modulating stimuli can be analyzed to serve as a feature associated with disease. Additionally physiological data obtained by an EEG sensor, an EOG sensor, and EMG sensor, or any combination thereof, can likewise be analyzed to obtain non-image-based features associated with disease. Non-image-based features associated with disease can then be outputted via 110. Potential inclusion of these non-image-based features associated with disease is indicated by the skip connection in the method 100 connecting step 104 to step 110. Outputted features associated with disease may be visualized on a suitable display (e.g. 226). Alternatively and/or additionally, these may be stored upon a processor 218, random access memory store 222, or a non-transient computer readable storage medium 224 for subsequent use.

Regarding step 114, features associated with disease may be interpreted as biomarkers indicative of one or more disease specific phenotypes. Features discussed herein are now placed into the context of these biomarkers. Features indicative of microvascular function may be obtained by spectral variance analysis, and may be interpreted to yield indications indicative of small vessel pathology. Regarding implementations involving the retina, alterations of microvascular function may be indicative of neurovascular pathology, which may be phenotypic of diseases including but not limited to: diabetic retinopathy, glaucoma, cerebrovascular small vessel disease, Alzheimer's disease, sickle cell disease, Parkinson's disease, Huntington's disease, and multiple sclerosis.

Features indicative of neuronal activity can likewise be obtained by virtue of spectral variance analysis and interpreted as biomarkers indicative of neuronal activity. Osmotic swelling, as observable by spectral variance analysis, may serve as a proxy to neuronal activity, thus allowing retinal responses to various stimuli to be observed. In this regard, the functional health of the retina can be revealed by interpreting these biomarkers indicative of neuronal activity.

Features indicative of axonal ultrastructure may likewise be interpreted to yield biomarkers indicative of disease-specific phenotypes. Pertaining to axonal ultrastructure, biomarkers obtained by computing one or more metrics of scatterer cylindricity and/or sphericity may include: mitochondrial fragmentation, axonal swelling, and axonal degeneration. Taken as a biomarker, mitochondrial fragmentation may be interpreted as being specific to diseases involving a metabolic component. Pertaining to implementations in which mitochondrial fragmentation is observed in the retinal nerve fiber layer, diseases indicated may include neurodegenerative diseases featuring a metabolic component, such diseases may include but are not limited to Alzheimer's disease, multiple sclerosis, glaucoma, and diabetic retinopathy. Axonal swelling, when taken as a biomarker, may indicate neurodegeneration involving a neuro-inflammatory component. Pertaining to the retina, axonal swelling therein may be associated with diseases including but not limited to Alzheimer's disease, multiple sclerosis, and glaucoma. Axonal degeneration, which may be observed in the retina, can be interpreted as an indication of advanced neurodegeneration. More generally, biomarkers indicative of axonal ultrastructure can yield indications indicative of tauopathies including but not limited to progressive supranuclear palsy, frontotemporal lobar degeneration, and Alzheimer's disease.

Features indicative of synaptic ultrastructure may be interpreted as biomarkers indicative of diseases known to affect the synaptic compartment. Specific biomarkers may include synaptic dropout, dendritic atrophy, and/or neuro-inflammation. Regarding implementations in which features indicative of synaptic ultrastructure are observed within the inner plexiform layer of the retina, these biomarkers may serve as subtle indications indicative of neurodegenerative diseases including but not limited to Alzheimer's disease and glaucoma, which are both known to affect both synapses and dendrites early in their progression.

Features indicative of axonal transport, as obtained via statistically characterizing speckle fluctuations and/or spectral variance analysis, may be interpreted as biomarkers indicative of neurodegeneration. In particular, axonal transport within the retinal nerve fiber layer is likely to become impaired early in the trajectory of diseases including but not limited to Alzheimer's disease, glaucoma, multiple sclerosis, and cerebral traumatic encephalopathy (CTE). Thus, obtaining biomarkers indicative of axonal transport within the retinal nerve fiber layer may be of predictive advantage in terms of diagnosing the aforementioned neurodegenerative diseases. Moreover, greater specificity may be afforded when assessing axonal transport in a cargo-specific manner (e.g. indications indicative of mitochondrial motility may be obtained). Further still, axonal transport can be interpreted as a salient biomarker of tauopathies, as mentioned above.

Features indicative of eye movements, and their response to saccade-modulating stimuli may likewise be interpreted as biomarkers indicative of disease. For example, diseases including but not limited to multiple sclerosis, CTE, and Alzheimer's disease may be indicated by biomarkers associated with eye movements. Moreover, in instances when saccade-modulating stimuli containing one or more spatially-varying contrast patterns is presented to a subject, features indicative of the contrast-sensitivity of a subject may be obtained. For example, a first saccade-modulating stimulus may include contrast that varies according to a different spatial frequency than a second saccade-modulating stimulus. Subject responsivity (e.g. eye movements) in response to the first and second saccade-modulating stimuli may then be compared to obtain biomarkers indicative of contrast sensitivity.

Via interpreting features indicated herein as biomarkers indicative of disease, one or more medical opinions can be rendered regarding the health of a subject; this is the goal of step 114 in method 100. In particular, the biomarkers outlined herein are of foreseeable utility with respect to diagnosing and monitoring neurodegenerative diseases including but not limited to Alzheimer's disease. Furthermore, these biomarkers, especially those pertaining to axonal transport, may be employed in settings involving investigations of therapeutic efficacy, such as clinical trials involving therapies seeking to monitor the efficacy of tau modifying therapies. Following the formation of one or more medical opinions, method 100 is concluded via END 116.

Figure 22:
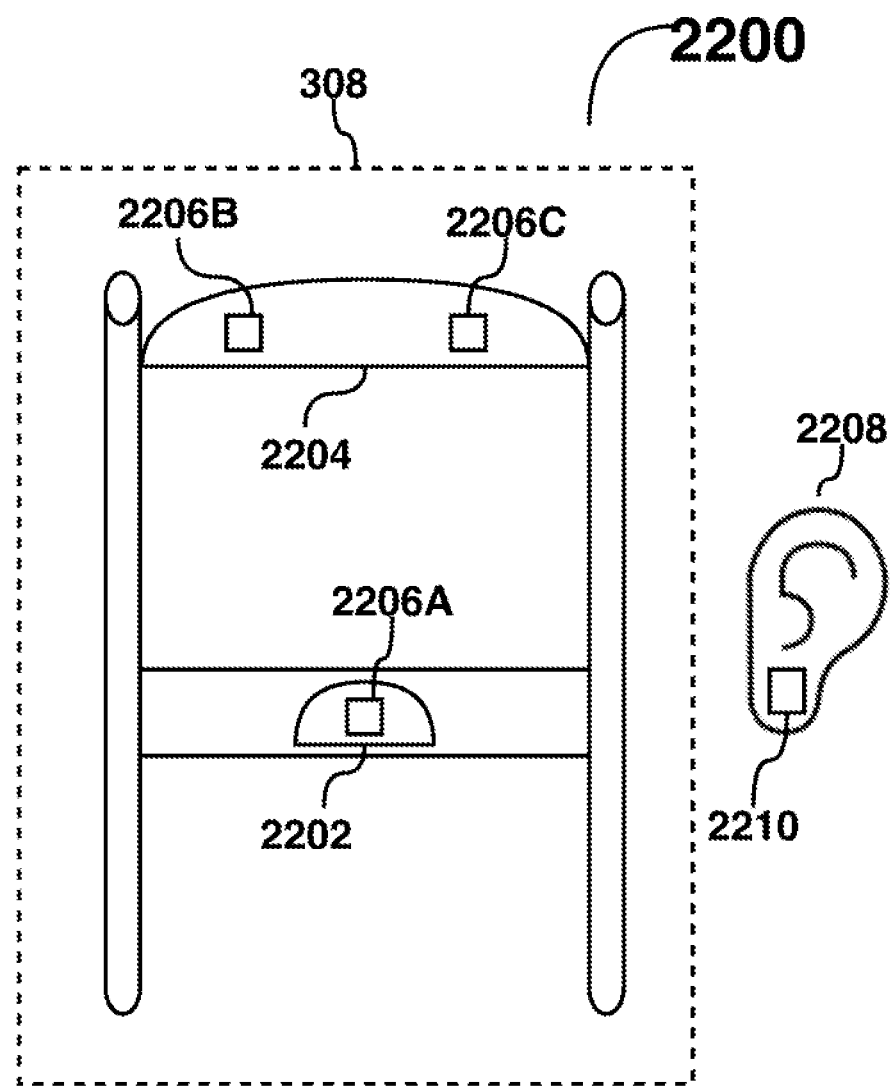
FIG. 22 is a schematic illustration of an eye positioning device including one or more sensors for generating physiological data associated with a subject, according to some implementations of the present disclosure.

Referring to FIG. 22, also disclosed herein is a device 2200 including a support frame intended to contact the head of a subject and position their eye relative to an imaging beam, and one or more sensors coupled to the support frame configured to generate physiological data from a subject. In certain implementations, the device 2200 can include an ophthalmic chinrest 308 integrated with one or more sensors. The device 2200 includes a first supporting component 2202 intended to support a first portion (e.g., chin) of the subject. The device 2200 also includes a second support 2204 component intended to support a second portion (e.g., the forehead of) the subject. The device 2200 further includes a plurality of skin-contacting sensors 2206A-2206C capable of generating physiological data from a subject. One or more of the sensors 2206A-2206C can be coupled to and/or located upon the first support component 2206, the second support component 2204, or both. In some implementations, the second support 2204 may house a plurality of skin-contacting EEG electrodes capable of recording biopotentials from the forehead of a subject. In these instances, a second one of the sensors 2206B may record a reference potential according to which potentials recorded electrode third sensor 2206C are referenced. Moreover, in other implementations, a first sensor 2206A on the first support 2202 may embody a skin-contacting electrode capable of recording biopotentials from the chin of a subject; in these implementations, the first sensor 2206A may provide an electrical reference according to which potentials recorded by the second sensor 2206B and the third sensor 2206C coupled to the second support 2204 may be referenced. In some implementations, a subject's ear 2208 may serve as the point of contact for a reference electrode 2204. In certain implementations, the device schematized in 2200 may contain one or more sensors capable of generating physiological data in the form of EEG data, EOG data, EMG data, or any combination thereof. Furthermore, the device 2200 may include a stimulus generator as described above (e.g., that is the same as, or similar to, the stimulus generator 302 described herein).

One or more elements or aspects or steps, or any portion(s) thereof, from one or more of any of claims 1-92 below can be combined with one or more elements or aspects or steps, or any portion(s) thereof, from one or more of any of the other claims 1-92 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:
    receiving, from one or more sensors, physiological data associated with a subject;
    generating spectral image data reproducible as one or more spectral images of a plurality of regions of interest in a sample, wherein the sample is an in-vivo tissue sample of the subject, the generating spectral image data including:
        determining whether a first portion of the physiological data satisfies a predetermined condition;
        causing a first fixation stimulus to be provided to a portion of the subject responsive to determining that the first portion the physiological data satisfies the predetermined condition;
        determining, based at least in part on a second portion of the physiological data that is associated with the subject subsequent to causing the first fixation stimulus to provided, whether the portion of the subject is fixated in response to the first fixation stimulus; and
        generating, in response to determining that the portion of the subject is fixated, a first portion of the spectral image data; and
    causing a stimulus generator to provide one or more stimuli to the subject to aid in reducing motion artifacts in the spectral image data.

2. The method of claim 1, wherein the one or more stimuli are provided to the subject based at least in part on the physiological data.

3. The method of claim 2, wherein the one or more sensors include an electroencephalographic (EEG) sensor, an electrooculographic (EOG) sensor, an electromyographic (EMG) sensor, a heart rate sensor, a pulse oximetry sensor, or any combination thereof.

4. The method of claim 1, wherein the sample includes at least a portion of an eye of a subject and the one or more stimuli include a saccade-modulating stimuli to aid in inhibiting movement of the eye of the subject.

5. The method of claim 1, wherein the generating the spectral image data further includes:
    verifying, based at least in part on the first image data, that the portion of the subject is fixated in response to the first fixation stimulus;
    causing a saccade-modulating stimulus to be provided to the portion of the subject responsive to the verifying; and
    generating, in response to the causing the saccade-modulating stimulus to be provided, a second portion of the spectral image data.

6. The method of claim 5, wherein generating the spectral image data further includes:
    causing a second fixation stimulus to be provided to the portion of the subject subsequent to generating a first portion of the second portion of the spectral image data and prior to generating a second portion of the second portion of the spectral image data.

7. The method of claim 1, further comprising receiving data indicative of a response by the subject to the one or more stimuli and the identifying the feature of interest is based at least in part on the data indicative of the response.

8. The method of claim 7, wherein the one or more stimuli are visual stimuli.

9. The method of claim 7, wherein the one or more visual stimuli contain one or more spatially-varying contrast patterns.

* * * * *